(12) United States Patent
Ferreira et al.

(10) Patent No.: US 11,234,741 B2
(45) Date of Patent: Feb. 1, 2022

(54) DEFORMABLE DEVICE FOR MINIMALLY INVASIVE FIXATION

(71) Applicant: Zimmer Biomet Spine, Inc., Westminster, CO (US)

(72) Inventors: Rui J. Ferreira, Livingston, NJ (US); Konstantin Caploon, Montclair, NJ (US)

(73) Assignee: Zimmer Biomet Spine, Inc., Westminster, CO (US)

(*) Notice: Subject to any disclaimer, the term of this patent is extended or adjusted under 35 U.S.C. 154(b) by 79 days.

(21) Appl. No.: 16/528,240

(22) Filed: Jul. 31, 2019

(65) Prior Publication Data
US 2020/0022732 A1 Jan. 23, 2020

Related U.S. Application Data

(63) Continuation of application No. 15/483,846, filed on Apr. 10, 2017, now Pat. No. 10,398,479, which is a
(Continued)

(51) Int. Cl.
| | | |
|---|---|---|
| *A61B 17/70* | (2006.01) | |
| *A61B 90/00* | (2016.01) | |
| *A61B 17/00* | (2006.01) | |

(52) U.S. Cl.
CPC ........ *A61B 17/708* (2013.01); *A61B 17/7002* (2013.01); *A61B 17/7032* (2013.01);
(Continued)

(58) Field of Classification Search
CPC .............. A61B 17/7032; A61B 17/708; A61B 17/7083–7089
See application file for complete search history.

(56) References Cited

U.S. PATENT DOCUMENTS

| | | |
|---|---|---|
| 4,386,603 A | 6/1983 | Mayfield |
| 4,733,657 A | 3/1988 | Kluger |
(Continued)

FOREIGN PATENT DOCUMENTS

| | | |
|---|---|---|
| EP | 553782 A1 | 8/1993 |
| WO | WO-2006091863 A2 | 8/2006 |
(Continued)

OTHER PUBLICATIONS

"U.S. Appl. No. 11/527,246, Non Final Office Action dated Sep. 15, 2010".
(Continued)

*Primary Examiner* — Eduardo C Robert
*Assistant Examiner* — Steven J Cotroneo
(74) *Attorney, Agent, or Firm* — Schwegman Lundberg & Woessner, P.A.

(57) ABSTRACT

The present teachings provide one or more surgical implements for repairing damaged tissue, such as through a fixation procedure. A system for a percutaneous procedure is provided. The system can include a bone fastener including a receiver. The system can include a device having a first end, a second end and a middle portion. The first end, middle portion and second end can be disposed along a longitudinal axis, and the second end can be connected to the receiver. The middle portion can have a pair of deformable leg members extending between the first and second ends. The leg members can define a channel having a width. The leg members can be selectively movable between a retracted state and an expanded state with the width of the channel greater in the expanded state than in the retracted state.

20 Claims, 12 Drawing Sheets

Related U.S. Application Data continuation of application No. 12/578,637, filed on Oct. 14, 2009, now Pat. No. 9,655,658.

(52) U.S. Cl.
CPC ...... *A61B 17/7049* (2013.01); *A61B 17/7088* (2013.01); *A61B 2017/00526* (2013.01); *A61B 2090/037* (2016.02)

(56) References Cited

U.S. PATENT DOCUMENTS

| | | | |
|---|---|---|---|
| 4,926,849 A | 5/1990 | Downey | |
| 4,957,495 A | 9/1990 | Kluger | |
| 5,219,349 A | 6/1993 | Krag et al. | |
| 5,354,292 A | 10/1994 | Braeuer et al. | |
| 5,728,046 A | 3/1998 | Mayer et al. | |
| 5,785,648 A | 7/1998 | Min | |
| 6,090,113 A | 7/2000 | Le Couedic et al. | |
| 6,123,707 A | 9/2000 | Wagner | |
| 6,139,549 A | 10/2000 | Keller | |
| 6,159,179 A | 12/2000 | Simonson | |
| 6,235,028 B1 * | 5/2001 | Brumfield | A61B 17/7083 606/53 |
| 6,287,313 B1 | 9/2001 | Sasso | |
| 6,530,929 B1 | 3/2003 | Justis et al. | |
| 6,562,046 B2 | 5/2003 | Sasso | |
| 6,648,888 B1 | 11/2003 | Shluzas | |
| 6,723,097 B2 | 4/2004 | Fraser et al. | |
| 6,749,613 B1 | 6/2004 | Conchy et al. | |
| 6,749,614 B2 | 6/2004 | Teitelbaum et al. | |
| 6,764,512 B2 | 7/2004 | Keller | |
| 6,821,277 B2 | 11/2004 | Teitelbaum | |
| 6,945,933 B2 | 9/2005 | Branch et al. | |
| 7,008,422 B2 | 3/2006 | Foley et al. | |
| 7,011,660 B2 | 3/2006 | Sherman et al. | |
| 7,056,321 B2 | 6/2006 | Pagliuca et al. | |
| 7,073,415 B2 | 7/2006 | Casutt et al. | |
| 7,160,300 B2 | 1/2007 | Jackson | |
| 7,250,052 B2 | 7/2007 | Landry et al. | |
| 7,465,306 B2 | 12/2008 | Pond, Jr. et al. | |
| 7,470,279 B2 | 12/2008 | Jackson | |
| 7,491,218 B2 | 2/2009 | Landry et al. | |
| 7,655,008 B2 | 2/2010 | Lenke et al. | |
| 7,695,475 B2 | 4/2010 | Justis et al. | |
| 8,197,446 B2 | 6/2012 | Beardsley | |
| 8,236,032 B2 | 8/2012 | Ramsay et al. | |
| 8,251,901 B2 * | 8/2012 | White | A61B 17/02 600/210 |
| 9,364,265 B2 | 6/2016 | Ramsay et al. | |
| 9,655,658 B2 | 5/2017 | Ferreria et al. | |
| 9,855,077 B2 | 1/2018 | Ramsay et al. | |
| 10,398,479 B2 | 9/2019 | Ferreira et al. | |
| 2002/0161368 A1 | 10/2002 | Foley et al. | |
| 2003/0009130 A1 | 1/2003 | Stecker et al. | |
| 2003/0208203 A1 | 11/2003 | Lim et al. | |
| 2004/0039384 A1 | 2/2004 | Frank, Jr. et al. | |
| 2004/0092939 A1 | 5/2004 | Freid et al. | |
| 2004/0138662 A1 | 7/2004 | Landry et al. | |
| 2004/0143265 A1 | 7/2004 | Landry et al. | |
| 2004/0147928 A1 | 7/2004 | Landry et al. | |
| 2004/0153064 A1 | 8/2004 | Foley et al. | |
| 2004/0158258 A1 | 8/2004 | Bonati et al. | |
| 2004/0172022 A1 | 9/2004 | Landry et al. | |
| 2004/0176665 A1 | 9/2004 | Branch et al. | |
| 2004/0215190 A1 | 10/2004 | Nguyen et al. | |
| 2005/0021031 A1 | 1/2005 | Foley et al. | |
| 2005/0038432 A1 | 2/2005 | Shaolian et al. | |
| 2005/0065517 A1 | 3/2005 | Chin | |
| 2005/0070917 A1 | 3/2005 | Justis | |
| 2005/0080418 A1 | 4/2005 | Simonson et al. | |
| 2005/0085813 A1 | 4/2005 | Spitler | |
| 2005/0090822 A1 | 4/2005 | Dipoto | |
| 2005/0131408 A1 | 6/2005 | Sicvol et al. | |
| 2005/0131420 A1 | 6/2005 | Techiera et al. | |
| 2005/0131421 A1 | 6/2005 | Anderson et al. | |
| 2005/0131422 A1 | 6/2005 | Anderson et al. | |
| 2005/0154389 A1 | 7/2005 | Selover et al. | |
| 2005/0171540 A1 | 8/2005 | Lim et al. | |
| 2005/0192485 A1 | 9/2005 | Branch et al. | |
| 2005/0192570 A1 | 9/2005 | Jackson | |
| 2005/0192589 A1 | 9/2005 | Raymond et al. | |
| 2005/0209694 A1 | 9/2005 | Loeb | |
| 2005/0245928 A1 | 11/2005 | Colleran et al. | |
| 2005/0277934 A1 | 12/2005 | Vardiman | |
| 2006/0004455 A1 | 1/2006 | Leonard et al. | |
| 2006/0052788 A1 | 3/2006 | Thelen et al. | |
| 2006/0069391 A1 | 3/2006 | Jackson | |
| 2006/0074418 A1 | 4/2006 | Jackson | |
| 2006/0074445 A1 | 4/2006 | Gerber et al. | |
| 2006/0079894 A1 | 4/2006 | Colleran et al. | |
| 2006/0079909 A1 | 4/2006 | Runco et al. | |
| 2006/0084993 A1 | 4/2006 | Landry et al. | |
| 2006/0095035 A1 | 5/2006 | Jones et al. | |
| 2006/0106380 A1 | 5/2006 | Colleran et al. | |
| 2006/0111712 A1 | 5/2006 | Jackson | |
| 2006/0111713 A1 | 5/2006 | Jackson | |
| 2006/0111714 A1 | 5/2006 | Foley | |
| 2006/0111715 A1 | 5/2006 | Jackson | |
| 2006/0122602 A1 | 6/2006 | Konieczynski et al. | |
| 2006/0149238 A1 | 7/2006 | Sherman et al. | |
| 2006/0200132 A1 | 9/2006 | Chao et al. | |
| 2006/0264950 A1 | 11/2006 | Nelson et al. | |
| 2006/0264962 A1 | 11/2006 | Chin et al. | |
| 2006/0276803 A1 * | 12/2006 | Salerni | A61B 17/7083 606/103 |
| 2006/0293693 A1 | 12/2006 | Farr et al. | |
| 2007/0073294 A1 | 3/2007 | Chin et al. | |
| 2007/0088258 A1 | 4/2007 | Wenchell et al. | |
| 2007/0093846 A1 | 4/2007 | Frigg et al. | |
| 2007/0106123 A1 | 5/2007 | Gorek et al. | |
| 2007/0191836 A1 | 8/2007 | Justis | |
| 2007/0191840 A1 | 8/2007 | Pond, Jr. et al. | |
| 2007/0233079 A1 | 10/2007 | Fallin et al. | |
| 2007/0276370 A1 | 11/2007 | Altarac et al. | |
| 2008/0015582 A1 | 1/2008 | Dipoto et al. | |
| 2008/0082103 A1 | 4/2008 | Hutton et al. | |
| 2008/0114403 A1 | 5/2008 | Kuester et al. | |
| 2008/0140120 A1 | 6/2008 | Hestad et al. | |
| 2008/0161857 A1 * | 7/2008 | Hestad | A61B 17/025 606/264 |
| 2008/0228228 A1 | 9/2008 | Hestad et al. | |
| 2008/0262318 A1 * | 10/2008 | Gorek | A61B 17/0206 600/235 |
| 2008/0275456 A1 * | 11/2008 | Vonwiller | A61B 17/7032 606/246 |
| 2008/0288003 A1 | 11/2008 | Mckinley | |
| 2008/0288005 A1 | 11/2008 | Jackson | |
| 2009/0082811 A1 | 3/2009 | Stad et al. | |
| 2009/0216328 A1 | 8/2009 | Birkmeyer et al. | |
| 2009/0221878 A1 * | 9/2009 | Gorek | A61B 17/0293 600/206 |
| 2009/0222044 A1 * | 9/2009 | Gorek | A61B 17/7085 606/279 |
| 2009/0228052 A1 | 9/2009 | Beardsley et al. | |
| 2009/0306721 A1 | 12/2009 | Kirschman | |
| 2010/0145267 A1 * | 6/2010 | Bishop | A61M 29/02 604/96.01 |
| 2011/0087293 A1 | 4/2011 | Ferreira et al. | |
| 2011/0166606 A1 | 7/2011 | Stihl et al. | |
| 2011/0196429 A1 * | 8/2011 | Hua | A61B 17/7083 606/279 |
| 2016/0106480 A1 | 4/2016 | Zhou et al. | |
| 2017/0209179 A1 | 7/2017 | Ferreira et al. | |

FOREIGN PATENT DOCUMENTS

| | | |
|---|---|---|
| WO | WO-2006116544 A3 | 11/2006 |
| WO | WO-2007035326 A3 | 3/2007 |
| WO | WO-2007087469 | 8/2007 |
| WO | WO-2008024937 A3 | 2/2008 |
| WO | WO-2008039460 A2 | 4/2008 |

(56) References Cited

FOREIGN PATENT DOCUMENTS

| WO | WO-2008130548 A1 | 10/2008 |
|---|---|---|
| WO | WO-2011046678 A1 | 4/2011 |

OTHER PUBLICATIONS

"U.S. Appl. No. 11/527,246, Final Office Action dated Mar. 1, 2011", 8 pgs.
"U.S. Appl. No. 11/737,819, Non Final Office Action dated Sep. 6, 2011", 8 pgs.
"U.S. Appl. No. 12/578,637, Advisory Action dated Mar. 8, 2016", 3 pgs.
"U.S. Appl. No. 12/578,637, Advisory Action dated Sep. 18, 2012", 2 pgs.
"U.S. Appl. No. 12/578,637, Examiner Interview Summary dated Jan. 11, 2012", 3 pgs.
"U.S. Appl. No. 12/578,637, Examiner Interview Summary dated Mar. 18, 2014", 3 pgs.
"U.S. Appl. No. 12/578,637, Examiner Interview Summary dated Jul. 17, 2012", 3 pgs.
"U.S. Appl. No. 12/578,637, Final Office Action dated May 15, 2012", 13 pgs.
"U.S. Appl. No. 12/578,637, Final Office Action dated Jul. 7, 2014", 18 pgs.
"U.S. Appl. No. 12/578,637, Final Office Action dated Nov. 20, 2015", 15 pgs.
"U.S. Appl. No. 12/578,637, Non Final Office Action dated May 8, 2015", 19 pgs.
"U.S. Appl. No. 12/578,637, Non Final Office Action dated Jul. 1, 2016", 6 pgs.
"U.S. Appl. No. 12/578,637, Non Final Office Action dated Nov. 1, 2011", 13 pgs.
"U.S. Appl. No. 12/578,637, Non Final Office Action dated Dec. 30, 2013", 15 pgs.
"U.S. Appl. No. 12/578,637, Notice of Allowance dated Jan. 9, 2017", 7 pgs.
"U.S. Appl. No. 12/578,637, Response filed Jan. 12, 2016 to Final Office Action dated Nov. 20, 2015", 15 pgs.
"U.S. Appl. No. 12/578,637, Response filed Feb. 1, 2012 to Non Final Office Action dated Nov. 1, 2011", 13 pgs.
"U.S. Appl. No. 12/578,637, Response filed Mar. 11, 2014 to Non Final Office Action dated Dec. 30, 2013", 14 pgs.
"U.S. Appl. No. 12/578,637, Response filed May 10, 2016 to Final Office Action dated Nov. 20, 2015", 14 pgs.
"U.S. Appl. No. 12/578,637, Response filed Aug. 10, 2015 to Non Final Office Action dated May 8, 2015", 14 pgs.
"U.S. Appl. No. 12/578,637, Response filed Aug. 14, 2012 to Final Office Action dated May 15, 2012", 13 pgs.
"U.S. Appl. No. 12/578,637, Response filed Aug. 27, 2014 to Final Office Action dated Jul. 7, 2014", 18 pgs.
"U.S. Appl. No. 12/578,637, Response filed Sep. 29, 2016 to Non Final Office Action dated Jul. 1, 2016", 9 pgs.
"U.S. Appl. No. 12/578,637, Response filed Oct. 20, 2011 to Restriction Requirement dated Oct. 4, 2011", 9 pgs.
"U.S. Appl. No. 12/578,637, Restriction Requirement dated Oct. 4, 2011", 6 pgs.
"U.S. Appl. No. 14/583,846, Response filed Oct. 24, 2018 to Non Final Office action dated Jul. 24, 2018", 9 pgs.
"U.S. Appl. No. 15/483,846, Non Final Office Action dated Jul. 24, 2018", 13 pgs.
"U.S. Appl. No. 15/483,846, Notice of Allowance dated Apr. 29, 2019", 9 pgs.
"U.S. Appl. No. 15/483,846, Preliminary Amendment filed Apr. 18, 2017", 7 pgs.
"U.S. Appl. No. 15/483,846, Response filed Mar. 20, 2018 to Restriction Requirement dated Feb. 7, 2018", 7 pgs.
"U.S. Appl. No. 15/483,846, Restriction Requirement dated Feb. 7, 2018", 6 pgs.
"European Application Serial No. 07838822.0, Extended European Search Report dated May 18, 2012", 7 pgs.
"International Application Serial No. PCT/US2007/020691, International Search Report dated Apr. 2, 2008", 3 pgs.
"International Application Serial No. PCT/US2008/004856, International Search Report dated Aug. 21, 2008", 3 pgs.
"International Application Serial No. PCT/US2008/004856, Written Opinion dated Aug. 21, 2008", 7 pgs.
"International Application Serial No. PCT/US2010/047084, International Preliminary Report on Patentability dated Apr. 26, 2012", 6 pgs.
"International Application Serial No. PCT/US2010/047084, International Search Report dated Mar. 29, 2011", 4 pgs.
"International Application Serial No. PCT/US2010/047084, Written Opinion dated Mar. 29, 2011", 4 pgs.

* cited by examiner

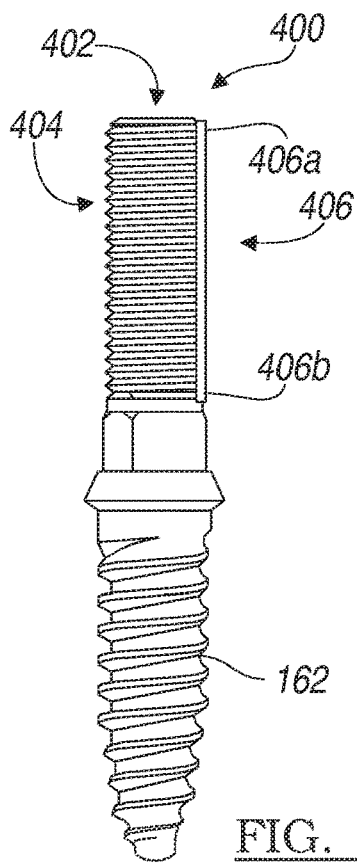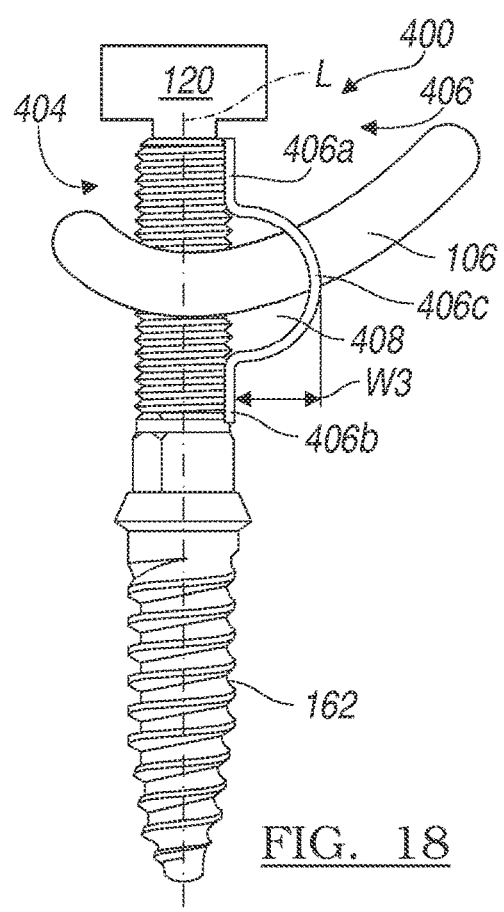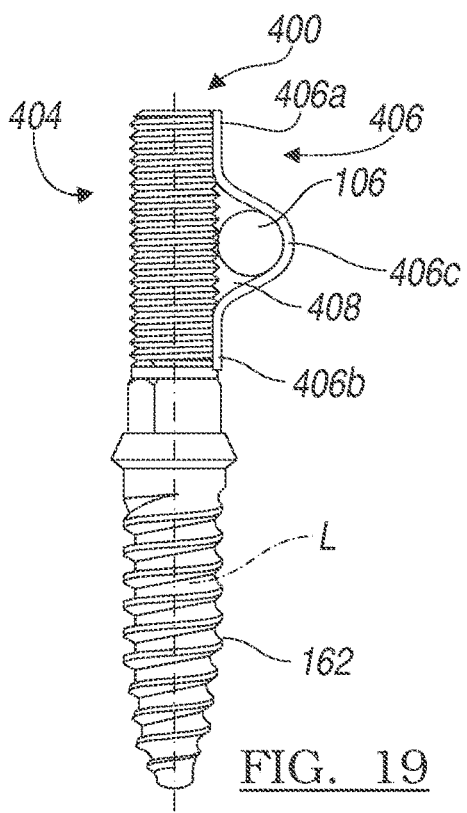
FIG. 17
FIG. 18
FIG. 19

DEFORMABLE DEVICE FOR MINIMALLY INVASIVE FIXATION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function or stabilize the damaged tissue, which can require the use of one or more orthopedic prosthesis, such as orthopedic nails, screws, implants, etc.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. Typically, a device can be used to couple the connecting device to each of the implants. The present teachings can provide a device for repairing damaged tissue, such as a deformable device for a minimally invasive fixation procedure.

A system for a percutaneous fixation procedure is provided. The system can include at least one bone fastener having a first end including a receiver and a second end adapted to engage an anatomy. The system can include at least one device. The at least one device can include a first end, a second end and a middle portion defined between the first end and the second end. The first end, middle portion and the second end can be disposed along a longitudinal axis, and the second end can be connected to the receiver. The middle portion can have a pair of deformable leg members, which can extend between the first end and the second end. The pair of deformable leg members can cooperate to define a channel having a width in a direction generally transverse to the longitudinal axis. The pair of deformable leg members can also be selectively movable between a retracted state and an expanded state such that the width of the channel is greater in the expanded state than the retracted state.

Provided is a system for a percutaneous fixation procedure. The system can comprise a connecting rod, and at least one device. The at least one device can include a first end and a second end being disposed along a longitudinal axis. The second end can be adapted to be coupled to a respective portion of the anatomy. The at least one device can include a deformable portion extending between the first end and the second end. The deformable portion can at least partially define a channel having a width in a direction generally transverse to the longitudinal axis. The deformable portion can be selectively movable between a retracted state and an expanded state such that the width of the channel is greater in the expanded state than in the retracted state. The width of the channel in the expanded state can be sized to accept at least a portion of the connecting rod through the channel.

A device for a percutaneous spinal fracture procedure utilizing a plurality of bone fasteners screwed to associated vertebra and a connecting rod connected to adjacent fasteners of the plurality of bone fasteners is also provided. The device can comprise a hollow tube having a proximal end and a distal end. The proximal end can be circumferentially closed, and the distal end can be for connection to a receiver of one of the plurality of bone fasteners. The hollow tube can further include a middle portion between the proximal end and distal end. The middle portion can have a pair of deformable leg members extending between the first and second ends. The pair of deformable leg members can cooperate to define a channel having a width in a direction generally transverse to the longitudinal axis, and the pair of deformable leg members can be movable between an expanded state and a retracted state such that the width of the channel is greater in the expanded state than in the retracted state.

In addition, a system for a percutaneous fixation procedure is provided. The system can include a connecting rod, and a bone fastener having a proximal end and a distal end disposed along a longitudinal axis. The distal end of the bone fastener can be adapted to engage an anatomy. The system can also include a deformable member carried by the proximal end of the bone fastener. The deformable member can cooperate with the proximal end to define a channel for receiving the connecting rod. The channel can have a width in a direction generally transverse to the longitudinal axis. The deformable member can be movable between a retracted state and an expanded state such that the width of the channel is greater in the expanded state than in the retracted state.

Further provided is a method of performing a percutaneous procedure. The method can include providing at least one device defining a channel having a first state and a second state. The channel can have a width in the first state that is less than a width of the channel in the second state. The method can also include coupling the at least one device to at least one implant coupled to an anatomy, and moving the channel of the at least one device from the first state to the second state. The method can include inserting a connecting rod through the channel of the at least one device, and moving the channel of the at least one device from the second state to the first state to couple the connecting rod to the at least one implant. The method can also include disconnecting the at least one device from the implant such that the connecting rod remains coupled to the at least one implant.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present invention will become more fully understood from the detailed description and the accompanying drawings.

FIG. 17 is a schematic illustration of a front view of another exemplary deformable device for use with a percutaneous fixation system for performing a minimally invasive fixation procedure in a first, retracted state;

FIG. 18 is a schematic illustration of a front view of the exemplary deformable device of FIG. 17 in a second, expanded state; and FIG. 19 is a schematic illustration of a front view of the exemplary deformable device of FIG. 17 in the retracted state, in which a portion of the connecting rod is coupled to the deformable device.

DESCRIPTION OF VARIOUS ASPECTS

Figure 1:
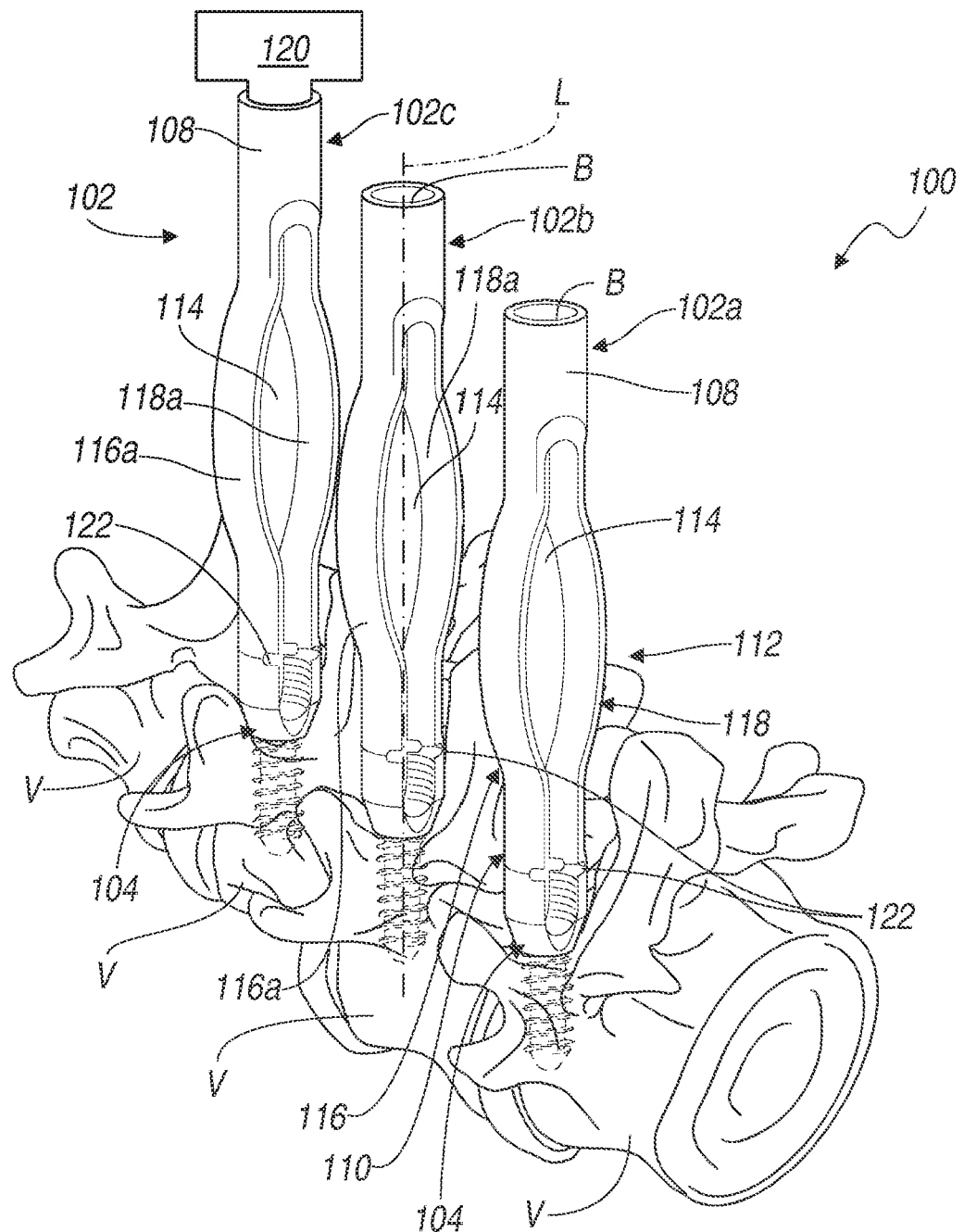
FIG. 1 is a schematic environmental illustration of a percutaneous fixation system for performing a minimally invasive fixation procedure according to the present teachings, which includes a plurality of exemplary deformable devices in a first, expanded state and coupled to a plurality of exemplary implants.

The following description is merely exemplary in nature and is not intended to limit the teachings, their application, or uses. It should be understood that throughout the drawings, corresponding reference numerals indicate like or corresponding parts and features. Although the following description is related generally to a method and apparatus for use in an anatomy to repair damaged tissue, such as in the case of spinal fusion, static spinal stabilization or dynamic spinal stabilization, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-12, a percutaneous fixation system is illustrated and generally identified at reference character 100. The percutaneous fixation system 100 may be particularly adapted for spinal fixation procedures. Various aspects of the present teachings, however, may have application for other procedures. The percutaneous fixation system 100 can enable a spinal procedure to be performed percutaneously in a minimally invasive manner. In certain applications, the percutaneous fixation system 100 can be coupled to one or more vertebrae or vertebral body V in a lumbar region of the spine, however, the percutaneous fixation system 100 can be used in other anatomical locations.

With reference to FIGS. 1-12, the percutaneous fixation system 100 can include a plurality of deformable devices or towers 102, a plurality of implants or bone anchors 104 and a connecting member or connecting rod 106. Generally, a tower 102 can be coupled to each bone anchor 104 to facilitate coupling the bone anchor 104 to the anatomy. The tower 102 can also be reconfigured to receive the connecting rod 106 so that the connecting rod 106 can be positioned into engagement with the bone anchor 104, as will be discussed. In addition, the tower 102 can form a portion of the implant or bone anchor 104, as will be discussed herein.

It should be noted that although the towers 102 are generally described and illustrated herein as being used to couple respective bone anchors 104 to the anatomy, it should be noted that the towers 102 can be used to remove or detach respective bone anchors 104 from the anatomy. Further, although the percutaneous fixation system 100 is generally illustrated and described herein as including three towers 102 each coupled to a respective bone anchor 104 for use with a single connecting rod 106, any combination of towers 102, bone anchors 104 and connecting rods 106 can be employed during a surgical procedure. For example, in a single level spinal fixation procedure, two towers 102 can be coupled to two bone anchors 104 to receive a single connecting rod 106. A multiple level spinal fixation procedure, however, will generally require additional towers 102 and bone anchors 104. In addition, it should be noted that although the towers 102 and bone anchors 104 are illustrated herein as being coupled to adjacent vertebral bodies V, the towers 102 and bone anchors 104 can be positioned so as to skip adjacent vertebral bodies V, if desired.

With reference to FIGS. 1-4, in one example, the towers 102 can include a first tower 102a, a second tower 102b and a third tower 102c. As each of the first tower 102a, the second tower 102b and the third tower 102c can be substantially identical, the same reference numerals will be used to describe the same parts or features, and the first tower 102a, the second tower 102b and the third tower 102c may be collectively referred to as the towers 102. Generally, the towers 102 can comprise hollow cylindrical tubes, which can be composed of a suitable biocompatible material, such as a metal, metal alloy or polymer, it should be noted, however, that the towers 102 can have any suitable shape for insertion into the anatomy, such as an hourglass, etc.

Each of the towers 102 can include a throughbore B, a first or proximal end 108, a second or distal end 110 and a deformable portion 112, A longitudinal axis L can be defined from the proximal end 108 to the distal end 110. Further, in the example of FIGS. 1-6, a channel 114 can be defined through the towers 102 from the proximal end 108 to the distal end 110 about a portion of the longitudinal axis. The formation of the channel 114 can result in the creation of a first leg member 116 and a second leg member 118, which extend generally parallel to the longitudinal axis, as will be discussed.

The bore B can extend from the proximal end 108 to the distal end 110. The bore B can be formed about the longitudinal axis L, and can enable surgical tools and devices to be passed through the towers 102, as will be discussed. The proximal end 108 can generally extend beyond the skin S of the patient when the tower 102 is fully inserted into the anatomy. The proximal end 108 can be configured to engage one or more tools 120 associated with the surgical procedure. Generally, the proximal end 108 can be circumferentially closed, however, the proximal end 108 could include notches, grooves, etc. to engage the tool 120, if desired. Particular tools 120 for use with the towers 102 are beyond the scope of the present teachings and need not be described herein.

Figure 2:
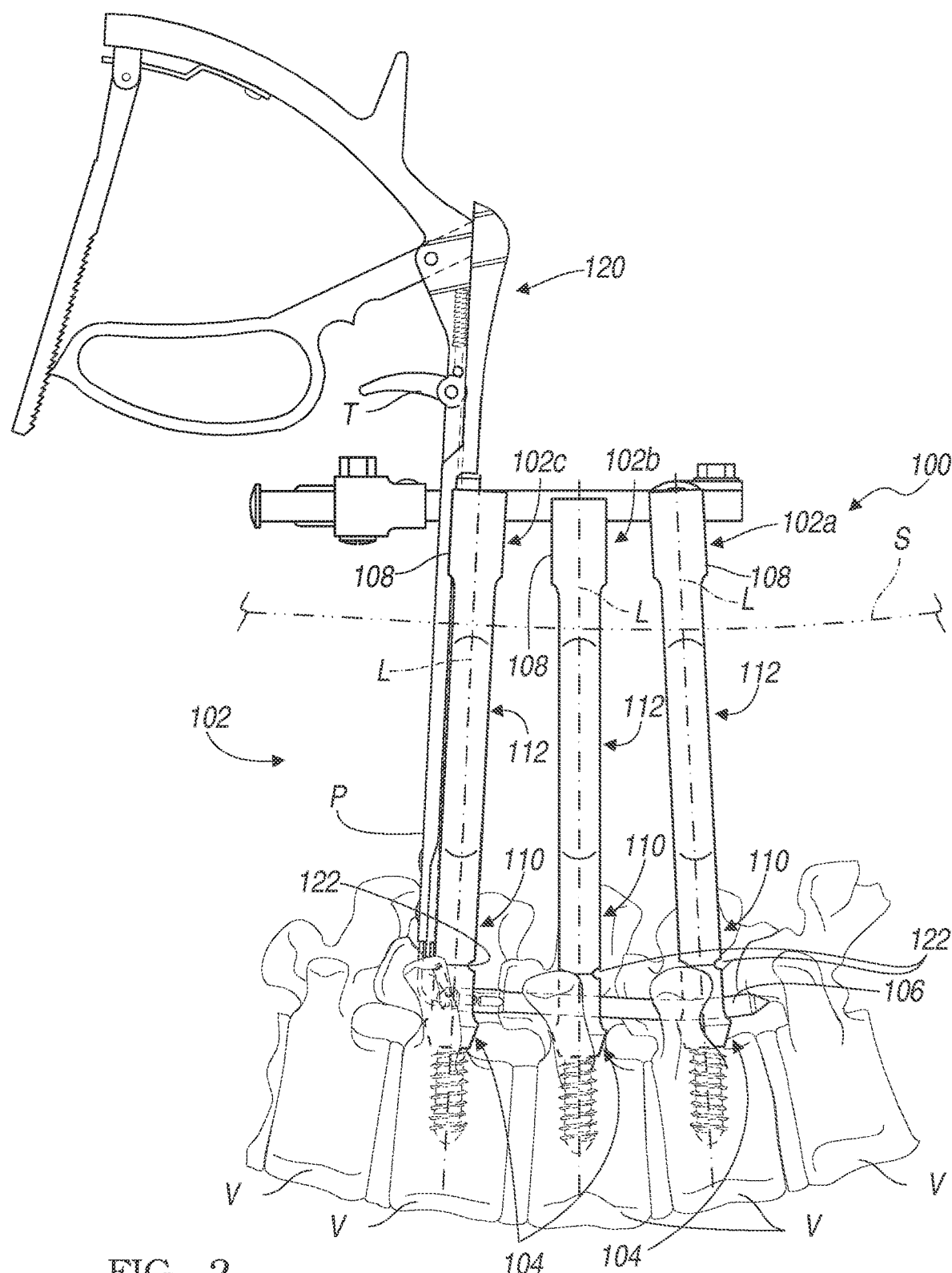
FIG. 2 is a side, environmental schematic illustration of the percutaneous fixation system of FIG. 1 including an exemplary tool for use in the insertion of the percutaneous fixation system into the anatomy.

Briefly, however, with reference to FIG. 2, an exemplary tool 120 is illustrated. In a conventional manner insofar as the present teachings are concerned, the tool 120 can be used to connect the towers 102 and the bone anchors 104 to a respective vertebral body V. The tool 120 can also be used to insert the connecting rod 106, as will be discussed in greater detail herein. Further detail regarding the tool 120 is outside the scope of the present application, but can be found in commonly owned U.S. Patent Publication No. 2008/0077138, filed on Apr. 20, 2007 and incorporated by reference herein. It should be noted that additional tools can be employed with the present teachings, such as those employed in the Polaris™ 5.5 Spinal System, commercially available from Biomet. Inc. of Warsaw, Ind.

In one example, as shown in FIGS. 1-6, the distal end 110 of the towers 102 can be circumferentially open at two locations due to the formation of the channel 114. Thus, the distal end 110 of the towers 102 can be defined by the first leg member 116 and the second leg member 118. The distal end 110 of the towers 102 can be coupled to the bone anchor 104.

In one example, as illustrated in FIGS. 1-6, the distal end 110 can be integrally, but frangibly, formed with the bone anchor 104. In this regard, a frangible notch 122 can be formed about at least a portion of the distal end 110 to enable the towers 102 to be removed or detached from the bone anchor 104 upon completion of the surgical procedure. For example, with reference to FIG. 3, the device 120 can be configured to apply a retractive or pulling force on the respective tower 102, which can cause the frangible notch 122 to fracture, thereby detaching the tower 102 from the bone anchor 104.

Figure 7:
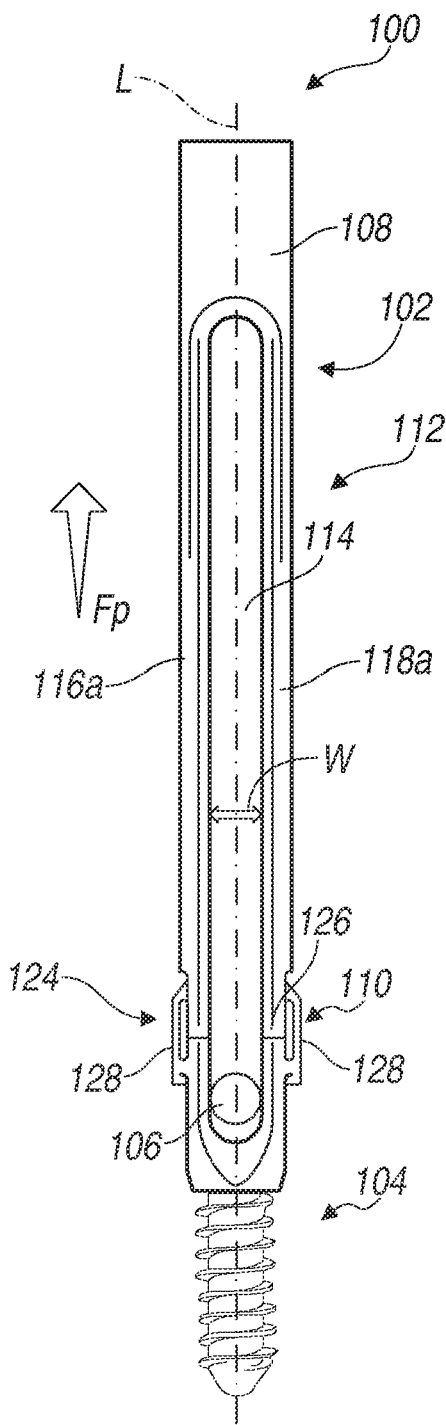
FIG. 7 is a schematic illustration of a front view of one of the plurality of exemplary deformable devices of FIG. 4 in the second, retracted state, illustrating an alternative exemplary connection between the plurality of exemplary deformable devices of FIG. 4 and the plurality of exemplary implants of FIG. 4.
Figure 8:
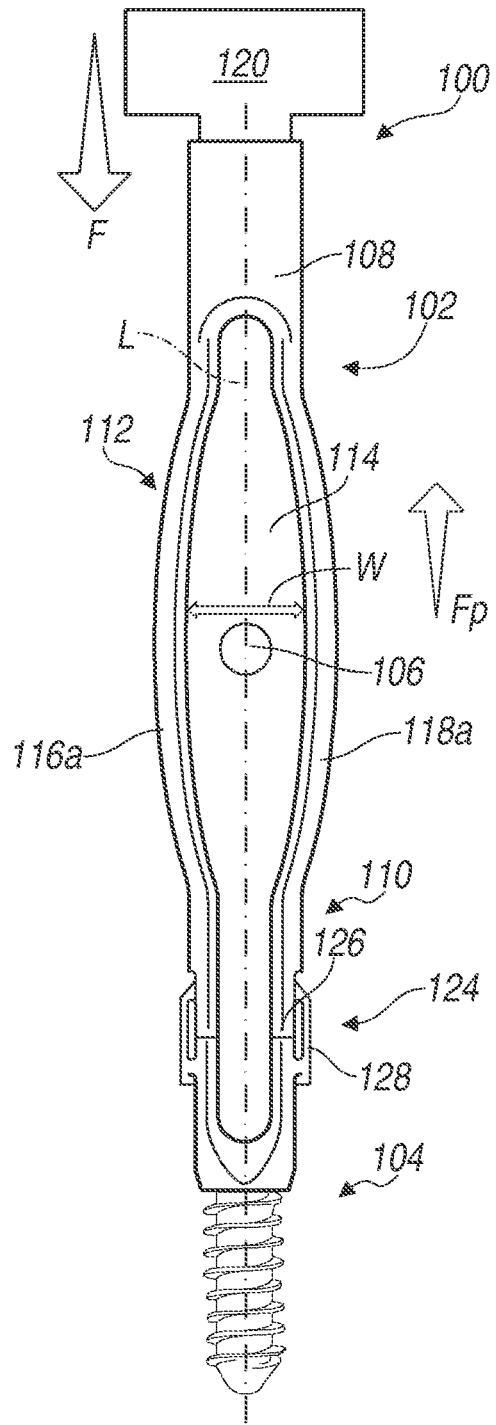
FIG. 8 is a schematic illustration of a front view of one of the plurality of exemplary deformable devices of FIG. 4 in the first expanded state, illustrating an alternative exemplary connection between the plurality of exemplary deformable devices of FIG. 4 and the plurality of exemplary implants of FIG. 4.

In a second example, with brief regard to FIGS. 7 and 8, the distal end 110 of the towers 102 can be coupled to the bone anchors 104 through a suitable mechanical connection, generally identified by reference numeral 124. In this example, the connection 124 can comprise an interference fit between a tapered portion 126 and an anchor extension 128. It should be noted that any connection 124 could be employed to releasably couple the towers 102 to the bone anchors 104, such as mating threads, mating keyed features, snap-fit, etc.

The tapered portion 126 can be formed on the distal end 110 of the towers 102, and thus, can comprise a portion of the first leg member 116 and second leg member 118. The anchor extension 128 can be coupled to the bone anchor 104. The anchor extension 128 can extend proximally or upwardly from the bone anchor 104 to define a cavity, which can receive the tapered portion 126. Thus, at the end of the surgical procedure, a suitable tool 120 can apply a retractive or pulling force $F_p$ to separate or detach the towers 102 from the bone anchors 104.

With reference back to FIGS. 1-6, the deformable portion 112 of the towers 102 can be formed between the proximal end 108 and distal end 110 of the towers 102, or at a middle portion or midsection of the towers 102. Generally, the deformable portion 112 can be defined on at least a portion of the first leg member 116 and the second leg member 118, and thus, can be formed about the channel 114. The deformable portion 112 can facilitate coupling the connecting rod 106 to the bone anchor 104 by changing a width W of the channel 114. The width W of the channel 114 can be defined in a direction transverse to the longitudinal axis L of the towers 102. The width W of the channel 114 can be changed by moving the deformable portion 112 between a retracted state and an expanded state.

Figure 5:
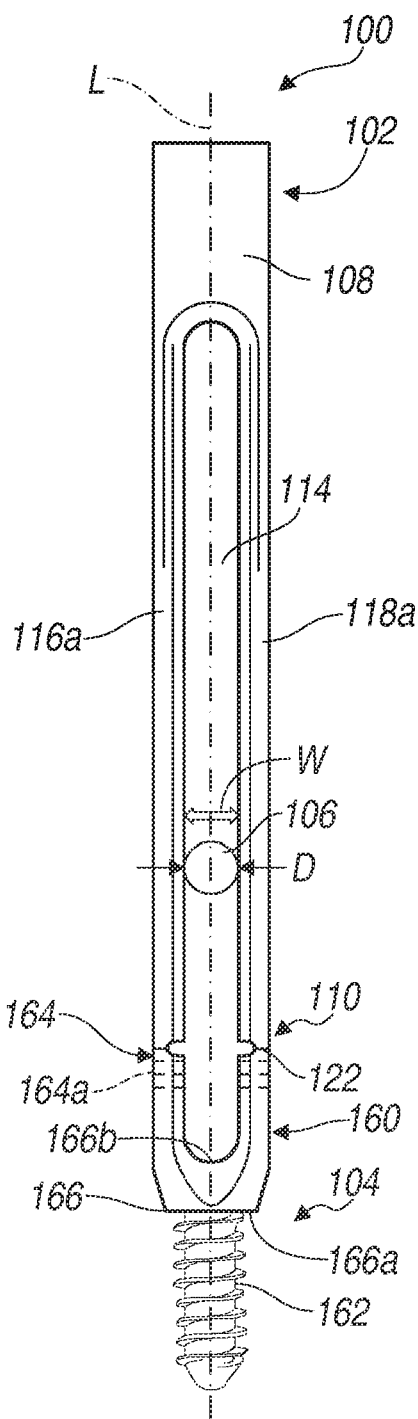
FIG. 5 is a schematic illustration of a front view of one of the plurality of exemplary deformable devices of FIG. 4 in the second, retracted state, illustrating a portion of the connecting rod coupled to one of the plurality of exemplary implants.
Figure 6:
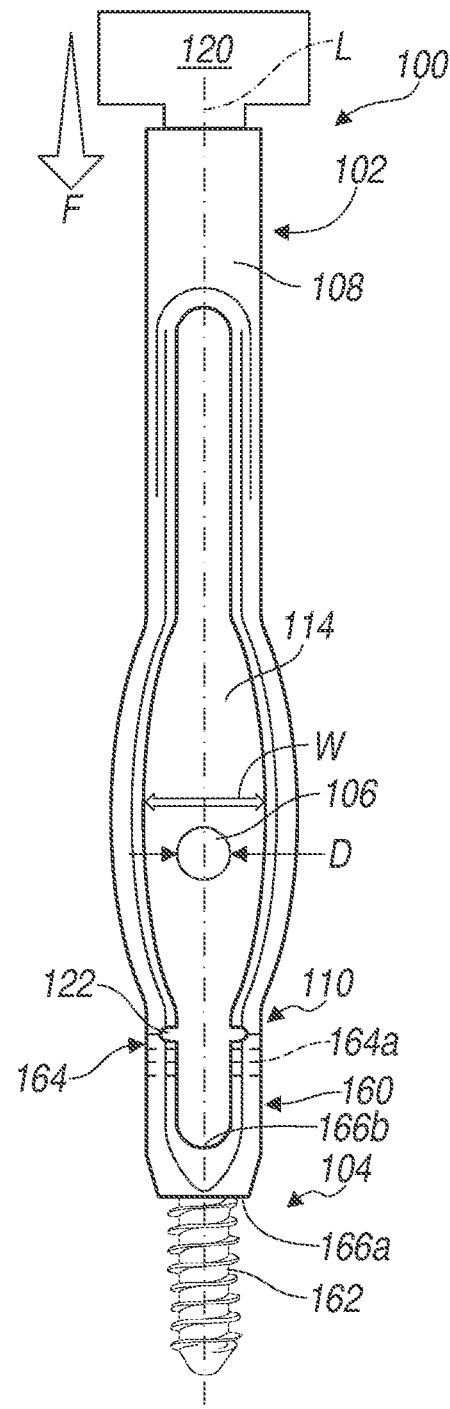
FIG. 6 is a schematic illustration of a front view of one of the plurality of exemplary deformable devices of FIG. 4 in the first, expanded state, illustrating a portion of the connecting rod inserted through the device.

In this regard, with reference to FIGS. 5 and 6, the deformable portion 112 can be selectively and reversibly movable between the retracted state and the expanded state. In the retracted state, the width W of the channel 114 can generally be about equal to or less than a diameter D of the connecting rod 106. In one example, the diameter D of the connecting rod 106 can be about 5.5 millimeters (mm). Thus, in the retracted state, the width W of the channel 114 can be about equal to or less than 5.5 millimeters (mm). In the expanded state, the width W of the channel 114 can be about greater than the diameter D of the connecting rod 106, and thus, the width W in the expanded state can be greater than about 5.5 millimeters (mm). In one example, the width W in the expanded state can range from about 5.5 millimeters to about 10 millimeters (mm). Thus, in certain applications, the width W in the expanded state can be greater than two times the width W of the channel 114 in the expanded state.

As shown in FIG. 6, the width W of the channel 114 in the expanded state can provide a larger passageway for the surgeon to maneuver the connecting rod 106 through the anatomy during a minimally invasive procedure. As will be discussed, the deformable portion 112 can be moved from the retracted state to the expanded state after the towers 102 are inserted into the anatomy. This can allow for a smaller incision to be made through the skin of the patient.

Figure 3:
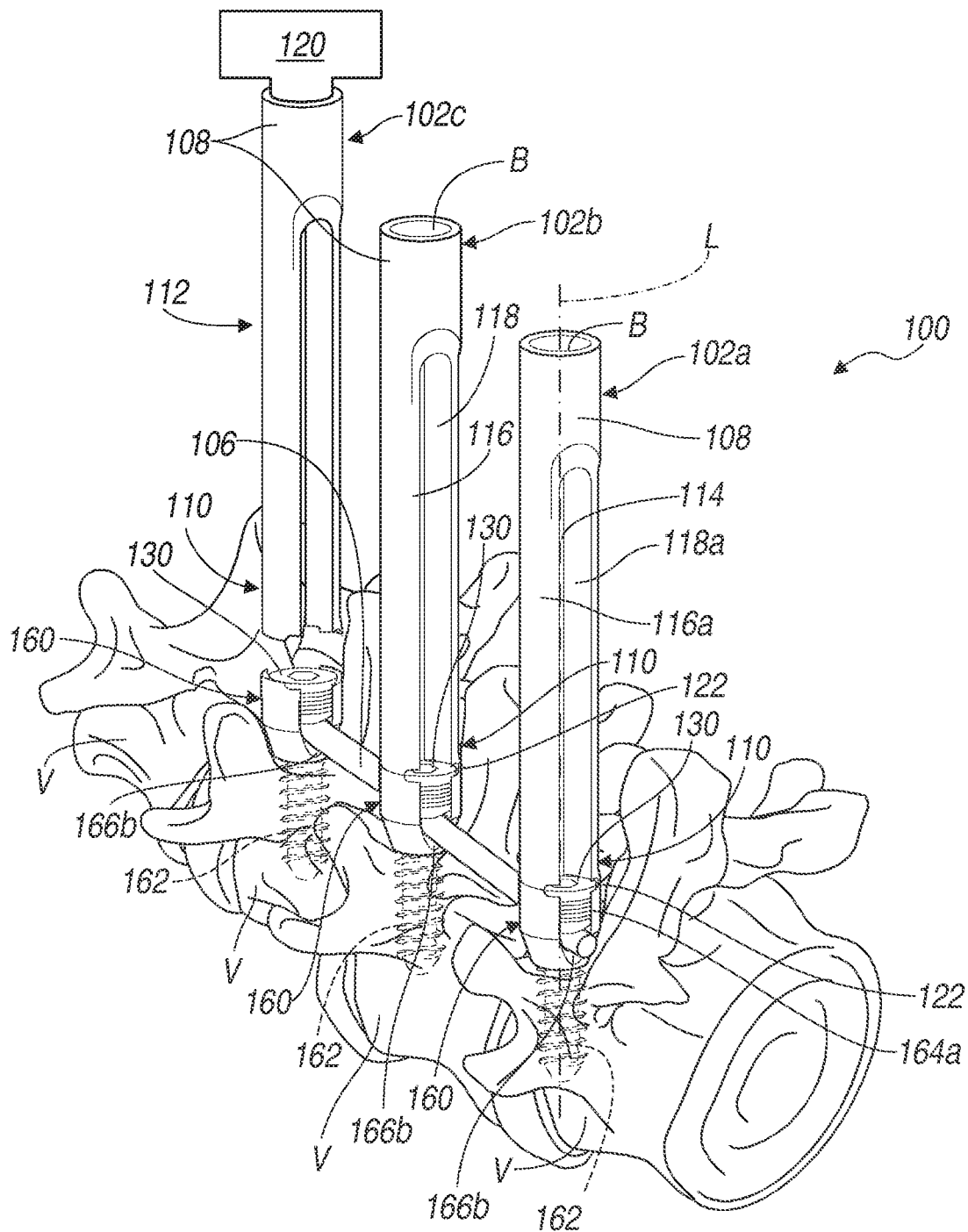
FIG. 3 is a schematic environmental illustration of the percutaneous fixation system of FIG. 1, in which the plurality of exemplary deformable devices are in a second, retracted state.
Figure 4:
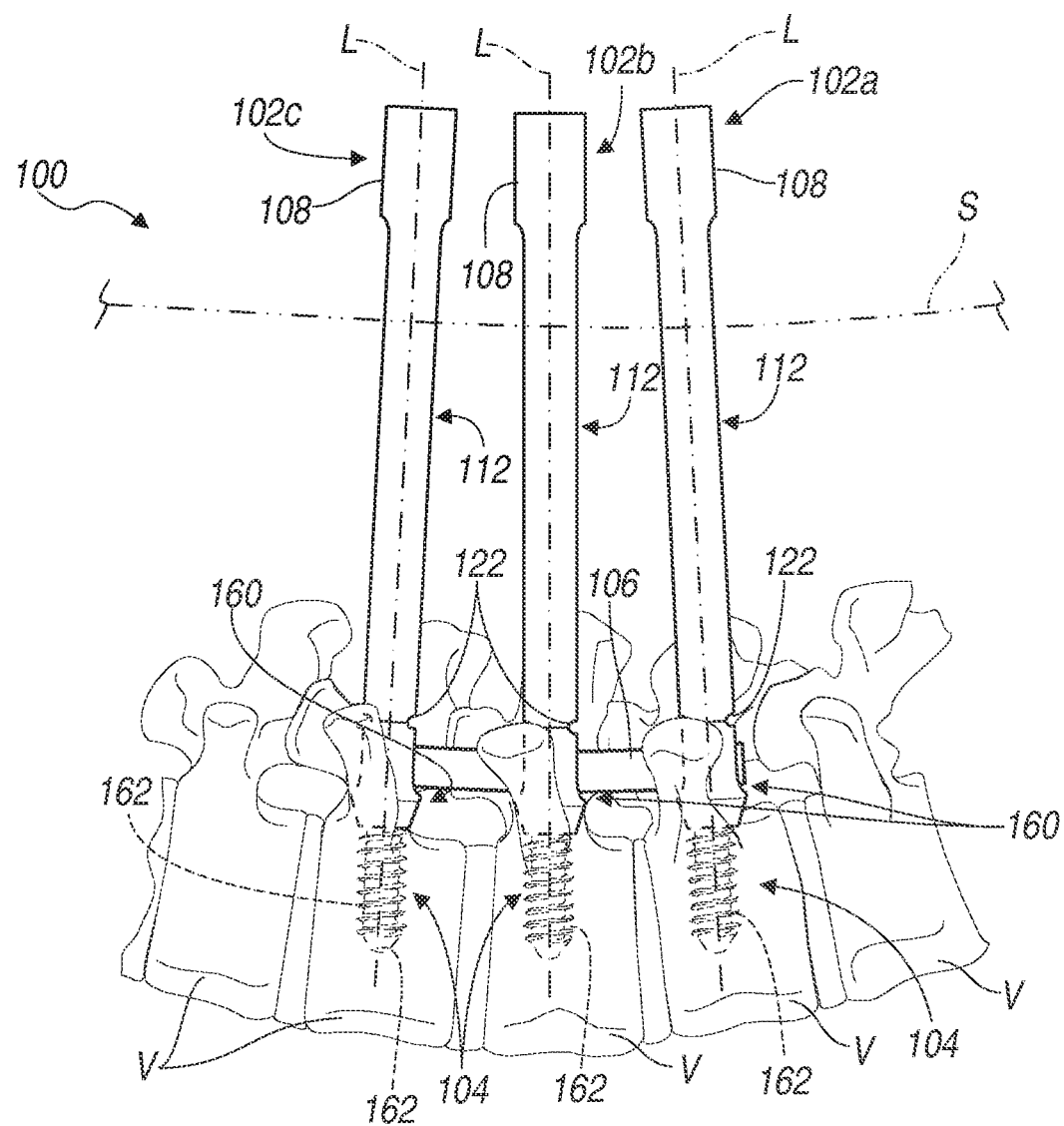
FIG. 4 is a side, environmental schematic illustration of the percutaneous fixation system of FIG. 1.

In addition, in cases where one or more adjacent vertebral bodies V are out of alignment or offset from each other, the larger passageway can allow the surgeon to couple the connecting rod 106 to each vertebral body V without requiring the surgeon to manually align the vertebral bodies V first. In other words, the width W of the channel 114 in the expanded state can allow the surgeon to couple the connecting rod 106 to each vertebral body V without requiring the surgeon to place each vertebral body V into alignment with each other. With reference to FIGS. 3 and 4, as will be discussed, once the connecting rod 106 is coupled to each of the vertebral bodies V, the deformable portion 112 can be moved from the expanded state to the retracted state. Upon movement of the deformable portion 112 from the expanded state to the retracted state, the connecting rod 106 can move each of the vertebral bodies V into alignment thereby correcting any alignment variance between the respective vertebral bodies V.

In one example, with reference to FIGS. 1-6, the deformable portion 112 can be formed along at least a portion of each of the first leg member 116 and second leg member 118, thereby forming a first deformable leg member 116a and a second deformable leg member 118a. Each of the first deformable leg member 116a and the second deformable leg member 118a can be movable relative to each other from the retracted state (FIG. 5) to the expanded state FIG. 6). The movement of the first deformable leg member 116a and the second deformable leg member 118a between the retracted state and the expanded state can increase or decrease the width W of the channel 114. Generally, the first deformable leg member 116a and the second deformable leg member 118a can expand outwardly away from each other in a direction transverse to the longitudinal axis.

The first deformable leg member 116a and the second deformable leg member 118a can move from the extracted state to the expanded state via any suitable mechanism. For example, with reference to FIG. 1, the tool 120 can be used to apply a downward compressive force F to one or more towers 102, which can cause the first deformable leg member 116a and the second deformable leg member 118a to bow outwardly into the expanded state. Alternatively, if the towers 102 are composed of a biocompatible shape memory alloy in which the expanded state is in "memory," then the tool 120 could apply heat or electrical current to one or more towers 102 to move the towers 102 into the "memoried" or expanded state.

Figure 9:
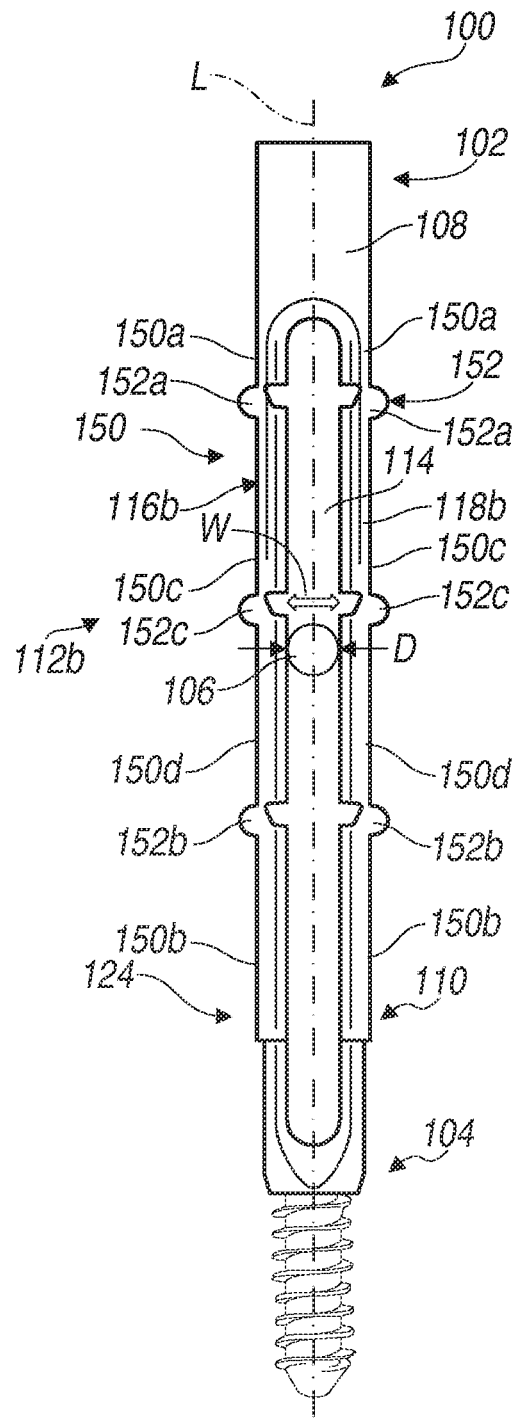
FIG. 9 is a schematic illustration of a front view of one of the plurality of exemplary deformable devices including an alternative deformable portion in the second, retracted state.
Figure 10:
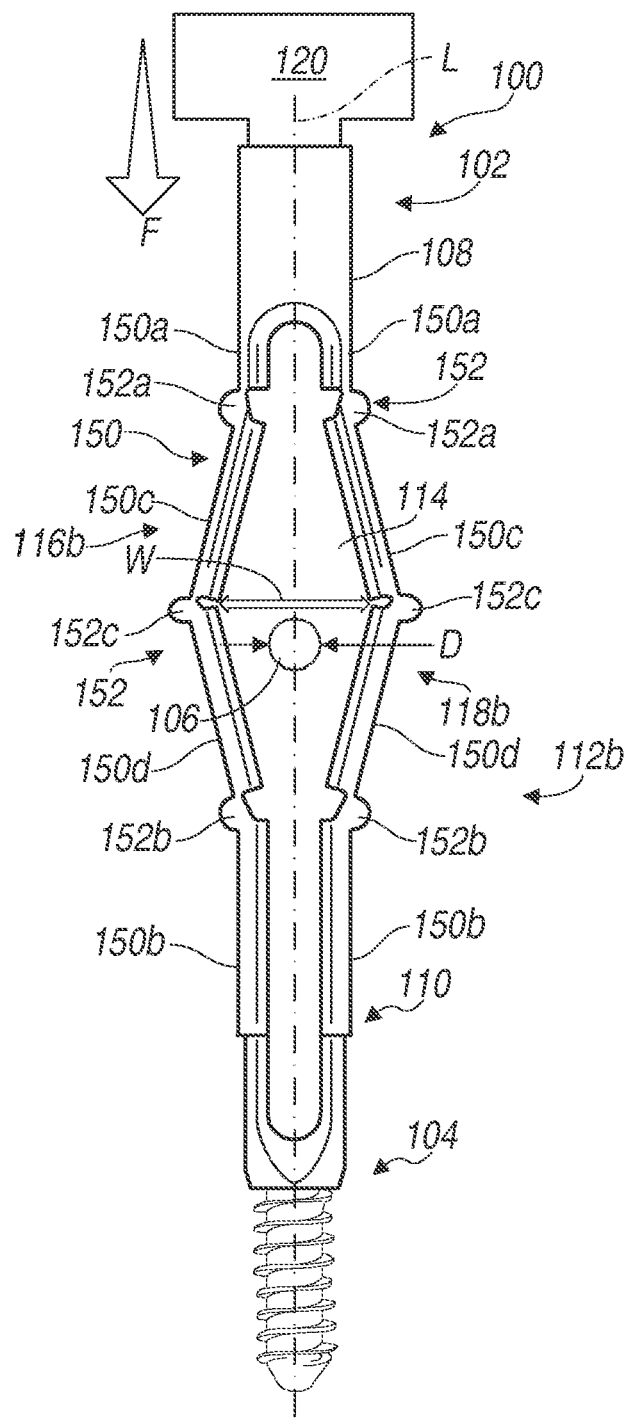
FIG. 10 is a schematic illustration of a front view of one of the plurality of exemplary deformable devices including an alternative deformable portion in the first, expanded state.

In another example, reference to FIGS. 9 and 10, a deformable portion 112b can include a first deformable leg member 116b and a second deformable leg member 118b. Each of the first deformable leg member 116b and the second deformable leg member 118b can be movable relative to each other from the retracted state to the expanded state. The movement of the first deformable leg member 116b and the second deformable leg member 118b between the retracted state and the expanded state can increase or decrease the width W of the channel 114. Generally, the first deformable leg member 116b and the second deformable leg member 118b can expand outwardly away from each other in a direction transverse to the longitudinal axis. As the first deformable leg member 116b and the second deformable leg member 118b can be substantially identical and symmetrical about the longitudinal axis L, the same reference numerals will be used to describe the same parts or features. The first deformable leg member 116b and the second deformable leg member 118b can each include at least one leg segment 150 and at least one hinge 152.

In the example of FIGS. 9 and 10, the first deformable leg member 116b and the second deformable leg member 118b can include a first leg segment 150a, a second leg segment 150b, a third leg segment 150c, a fourth leg segment 150d, a first hinge 152a, a second hinge 152b and a third hinge 152c. It should be understood that this combination of leg segments 150 and hinges 152 is merely exemplary, as the first deformable leg member 116b and the second deformable leg member 118b could include any desired number of leg segments 150 and hinges 152, such as two leg segments 150 and a single hinge 152. In addition, the leg segments 150 and hinges 152 can generally be integrally formed with the tower 102, with the hinges 152 being machined or molded from a portion of the first deformable leg member 116b and the second deformable leg member 118b to define the leg segments 150. It should be noted, however, that any suitable manufacturing technique could be used to form the leg segments 150 and hinges 152.

The first leg segment 150a can be coupled at one end to the proximal end 108 of the tower 102, and can be coupled at an opposite end to the first hinge 152a. Generally, the first leg segment 150a can remain somewhat stationary as the deformable portion 112b moves between the retracted state (FIG. 9) and expanded state (FIG. 10). The second leg segment 150b can be coupled at one end to a portion of the bone anchor 104, and can be coupled at an opposite end to the second hinge 152b. The second leg segment 150b can also remain somewhat stationary as the deformable portion 112b moves between the retracted state (FIG. 9) and expanded state (FIG. 10). The third leg segment 150c can be coupled at one end to the first hinge 152a, and can be coupled at an opposite end to the third hinge 152O. The third leg segment 150O can generally be movable relative to the first leg segment 150a via the first hinge 152a. The fourth leg segment 150d can be coupled at one end to the third hinge 152c, and can be coupled at an opposite end to the second hinge 152b. The fourth leg segment 150d can move relative to the second leg segment 150b, via the second hinge 152b, and can move relative to the third leg segment 150c, via the third hinge 152c.

The third leg segment 150O can also move relative to the fourth leg segment 150d via the third hinge 152c. The movement of the third leg segment 1590 and the fourth leg segment 150d about the first hinge 152a, second hinge 152b and the third hinge 152c can move the first deformable leg member 116b and the second deformable leg member 118b between the expanded state (FIG. 10) and retracted state (FIG. 9). Generally, the third leg segment 150c and the fourth leg segment 150d can move to define acute angles relative to the longitudinal axis L when the towers 102 are in the expanded state (FIG. 10).

The first deformable leg member 116b and the second deformable leg member 118b can move from the retracted state (FIG. 9) to the expanded state (FIG. 10) via any suitable mechanism. For example, the tool 120 can be used to apply a downward compressive force F to one or more towers 102, which can cause the third leg segment 150c and the fourth leg segment 150d to move about the first hinge 152a, second hinge 152b and the third hinge 152c in an outward direction generally transverse to the longitudinal axis L. The outward movement of the third leg segment 150c and the fourth leg segment 150d into the expanded state can increase the width of the channel 114 to provide the larger passageway for acceptance of the connecting rod 106.

With reference to FIGS. 1-12, a bone anchor 104 can be coupled to the distal end 110 of each of the towers 102. An exemplary bone anchor 104 can be substantially similar to the multi-axial screws employed in the Polaris™ 5.5 Spinal System, commercially available from Biomet, Inc. of Warsaw, Ind., or the bone fastener disclosed in commonly owned U.S. Patent Publication No. 2008/0077138, filed on Apr. 20, 2007 and previously incorporated by reference herein. As the bone anchor 104 can be generally known, the bone anchor 104 will not be discussed in great detail herein. Briefly, however, with reference to FIGS. 5 and 6, the bone anchor 104 can include a tulip head or saddle 160 and a bone engaging member or bone fastener 162.

The saddle 160 can be substantially U-shaped, and can include a first or proximal end 164 and a second or distal end 166. The proximal end 164 can be releasably coupled to the distal end 110 of the tower 102, and can define a mating portion 164a. The mating portion 164a can be configured to receive a fastening mechanism to couple the connecting rod 106 to the saddle 160. In one example, the mating portion 164a can comprise a plurality of threads, which can matingly engage threads formed on a set screw 130 to couple the connecting rod 106 to the bone anchor 104 (FIG. 3).

The distal end 166 can define an aperture 166a and a receiver 166b. The aperture 166a can be sized to enable a distal end of the bone fastener 162 to pass through the saddle 160, while a head or a proximal end of the bone fastener 162 is coupled to the saddle 160. The receiver 166b can comprise generally arcuate surfaces formed by the U-shape of the saddle 160. The receiver 166b can be sized and configured to receive at least a portion of the connecting rod 106.

The bone fastener 162 can include the head or proximal end and the distal end. The proximal end can be configured to retain the bone fastener 162 within the saddle 160. The distal end can be configured to engage the anatomy to secure the bone fastener 162 to the anatomy. In one example, the distal end can include a plurality of threads.

The connecting rod 106 can be received within the receiver 166b of the saddle 160. As will be discussed, the connecting rod 106 can be guided into the receiver 166b via the towers 102. An exemplary connecting rod 106 can be substantially similar to the connecting rod employed in the Polaris™ 5.5 Spinal System, commercially available from Biomet, Inc. of Warsaw, Ind., or the connecting element disclosed in commonly owned U.S. Patent Publication No. 2008/0077138, filed on Apr. 20, 2007 and previously incorporated by reference herein. As the connecting rod 106 can be generally known, the connecting rod 106 will not be discussed in great detail herein. Briefly, however, the connecting rod 106 can comprise an elongated solid cylindrical tube. The connecting rod 106 can also include a slight curvature, which can correspond to the natural curvature of the spine. Typically, the connecting rod 106 can be composed of a suitable biocompatible material having sufficient rigidity to fix the vertebral bodies V relative to each other.

In this regard, in order to fix the vertebral bodies V in a spinal fixation procedure, each tower 102 can be integrally, but frangibly, coupled to each bone anchor 104, as shown in FIGS. 1-6, or each tower 102 can be coupled to each bone anchor 104 via the connection 124, as shown in FIGS. 7 and 8. It should be noted that various combinations of the connection 124 or the frangible notch 122 can be used in a single surgical procedure, if desired. With the towers 102 coupled to respective bone anchors 104, surgical access can be made through the skin S adjacent to the vertebral bodies V of interest (FIGS. 2 and 4). The specific surgical access approaches are beyond the scope of the present application, but for example, surgical access can be obtained via a minimally invasive surgical procedure. Exemplary manners or surgical procedures can include that used with the Polaris™ 5.5 Spinal System, commercially available from Biomet, Inc. of Warsaw, Ind., the minimally invasive surgical procedure disclosed in commonly owned U.S. Patent Publication No. 2008/0077138, filed on Apr. 20, 2007 and previously incorporated by reference herein. Fascia splitting and other known techniques may also be used with the present teachings.

Figure 11:
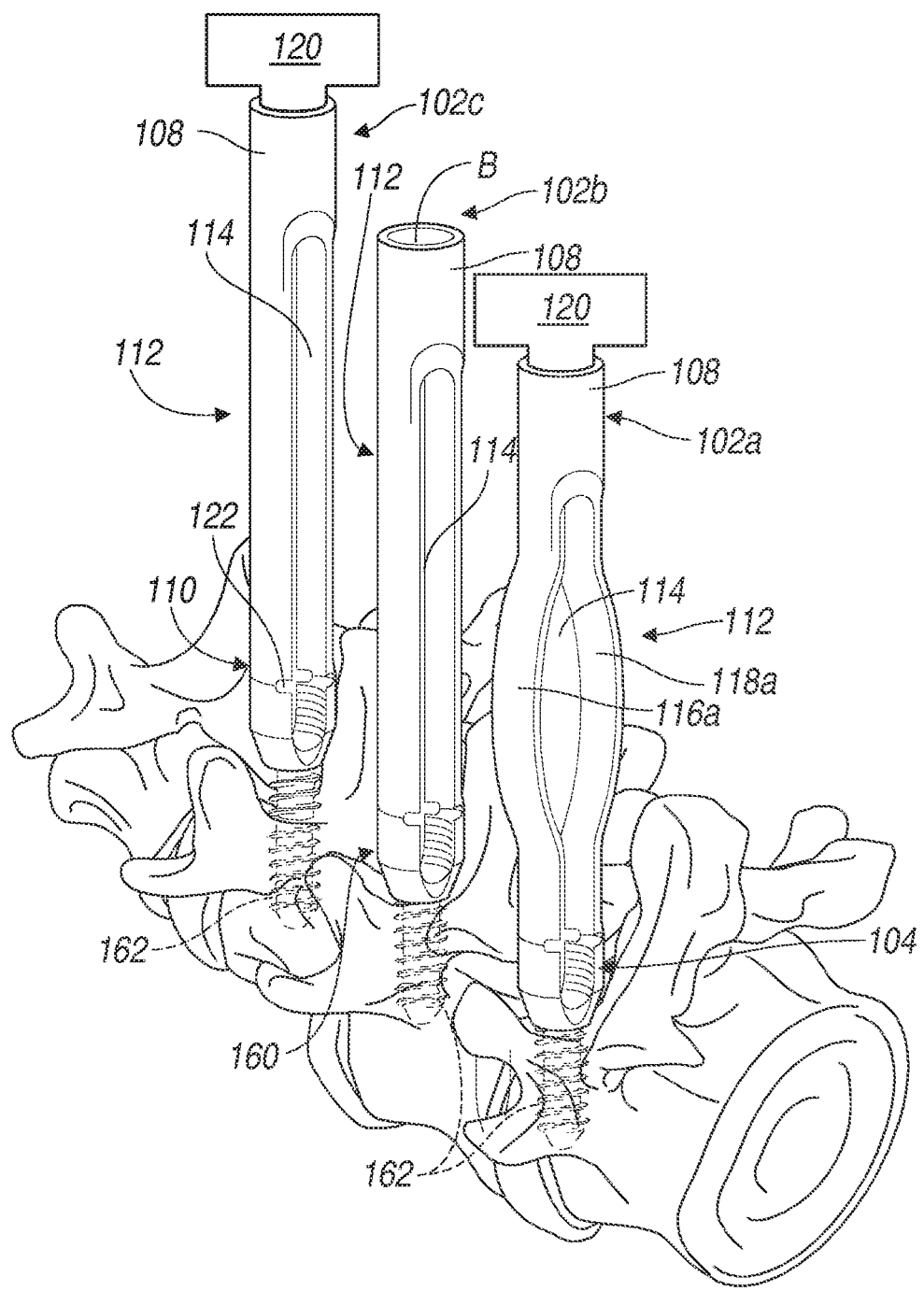
FIG. 11 is a schematic environmental illustration of a step of one of various methods for coupling the plurality of exemplary deformable devices of FIG. 1 to the anatomy.

With surgical access to the vertebral bodies V established, the tower 102 and bone anchor 104 can be inserted into the anatomy. Note that each tower 102 can be inserted into the anatomy in the retracted state. In one example, as discussed in commonly owned U.S. Patent Publication No. 2008/0077138, previously incorporated by reference herein, a guidewire can be used to direct each tower 102 and bone anchor 104 into a proper position on a pedicle of each vertebral body V. With reference to FIG. 11, once properly positioned, a suitable tool 120 can be used to secure the bone fastener 162 of each bone anchor 104 to the vertebral body V. With each bone anchor 104 secured, each tower 102 can be moved from the retracted state to the expanded state via a suitable tool 120.

Figure 12:
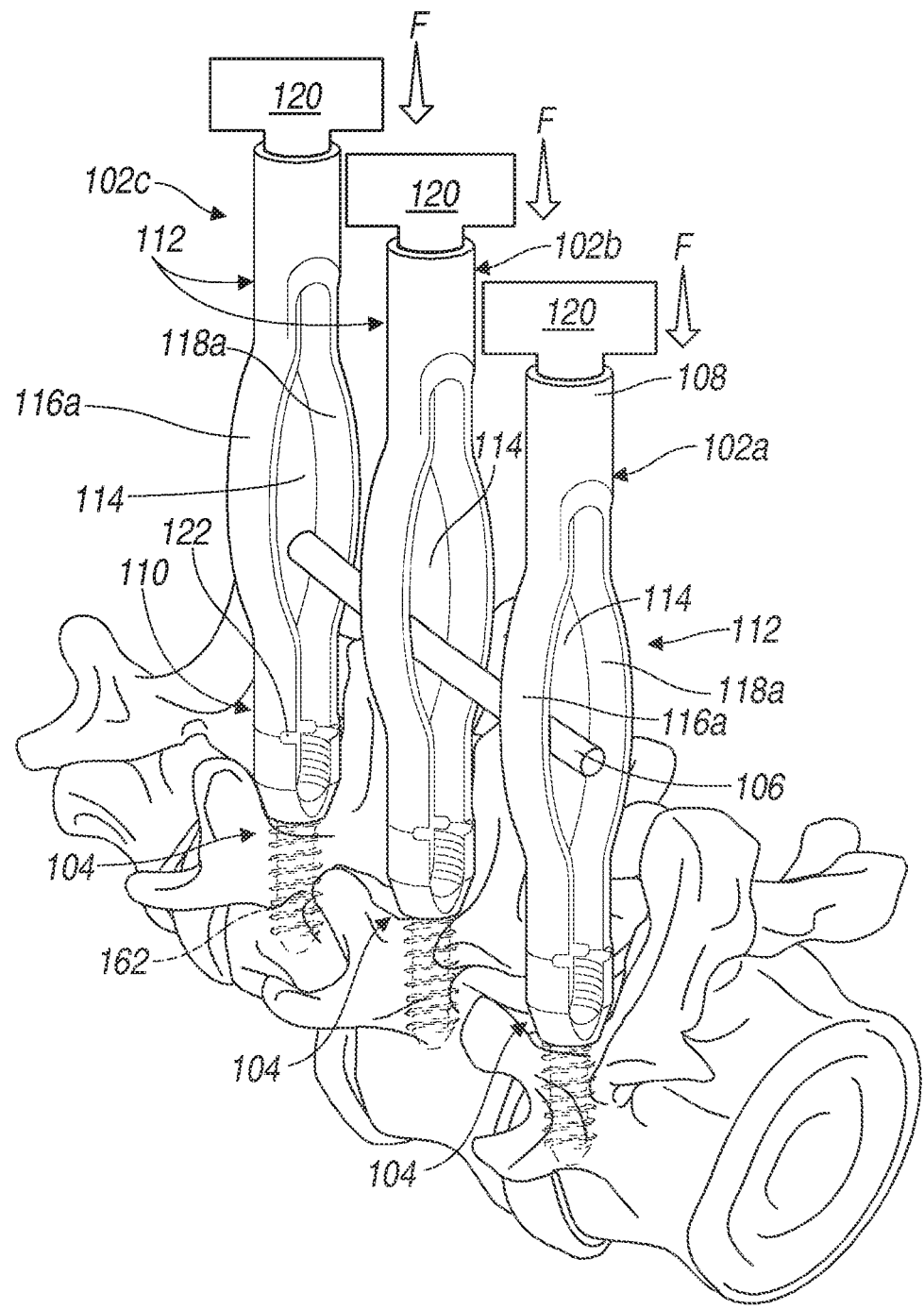
FIG. 12 is a schematic environmental illustration of a step of one of various methods for coupling the connecting rod to the plurality of exemplary deformable implants via the plurality of exemplary deformable devices of FIG. 1.

In order to move the first deformable leg member 116a and the second deformable leg member 118a of the deformable portion 112 into the expanded state, with reference to FIG. 12, the tool 120 can apply the compressive force F to the proximal end 108 of the tower 102. Alternatively, if the tower 102 is composed of a shape memory material, the tool 120 can apply heat or electric current to the tower 102 to move the first deformable leg member 116a and the second deformable leg member 118a into the expanded state. In another example, if the tower 102 includes the deformable portion 112b (FIGS. 9 and 10), the tool 120 can apply a compressive force to the proximal end 108 of the tower 102 to cause the third leg segment 150c and fourth leg segment 150d to move relative to the first leg segment 150a and second leg segment 150b about the hinges 152 into the expanded state. Note that the towers 102 can be moved into the expanded state in any sequence, individually, or at once.

With each of the towers 102 in the expanded state, the connecting rod 106 can easily be inserted into the channels 114 having the wider width W, as shown in FIG. 12. Various techniques can be used to insert the connecting rod 106 through the towers 102. In one example, the connecting rod 106 can be introduced into the anatomy via a small incision and guided through the towers 102 using a suitable tool. In an alternative example, the towers 102 can include circumferentially open proximal ends 108, and the connecting rod 106 can be inserted through an elongate incision directly into the channels 114 of the towers 102 (also known as fascia splitting). In another of various examples, the connecting rod 106 can be inserted through the towers 102 using the exemplary tool 120, as illustrated in FIG. 2. In this example, a percutaneous rod inserter P can be coupled to the tool 120, which can be actuated via a trigger T to insert the connecting rod 106 into the channels 114, as described in commonly owned U.S. Patent Publication No. 2008/0077138, filed on Apr. 20, 2007 and previously incorporated by reference herein.

With reference to FIG. 3, once the connecting rod 106 is inserted through each of the channels 114, the connecting rod 106 can be positioned into the receiver 160a of the saddle 160. Next, the towers 102 can be moved from the expanded state to the retracted state. Note that the towers 102 can be moved from the expanded state to the retracted state in any order or combination, such as one at a time, all at once, etc. The tool 120 can be used to move the towers 102 from the expanded state to the retracted state by removing the compressive force F, removing the heat or current, etc.

With the connecting rod 106 positioned within the receivers 160a and the towers 102 in the retracted state, the set screws 130 can be inserted through the bore B of each tower 102. The set screws 130 can be rotated with a suitable tool 120 into engagement with the mating portion 164 of the saddle 160 to secure the connecting rod 106 to the bone anchor 104.

Next, the towers 102 can be detached from the bone anchors 104. In one example, the frangible portion 122 of the towers 102 can be broken to separate the towers 102 from the bone anchors 104 (FIG. 3), or the tapered portion 126 of the towers 102 can be disengaged with the anchor extension 128 of the bone anchors 104 (FIGS. 7 and 8). Once the towers 102 are disengaged from the bone anchors 104, the surgical access site can be closed or additional surgical procedures can be performed, if desired.

Figure 13:
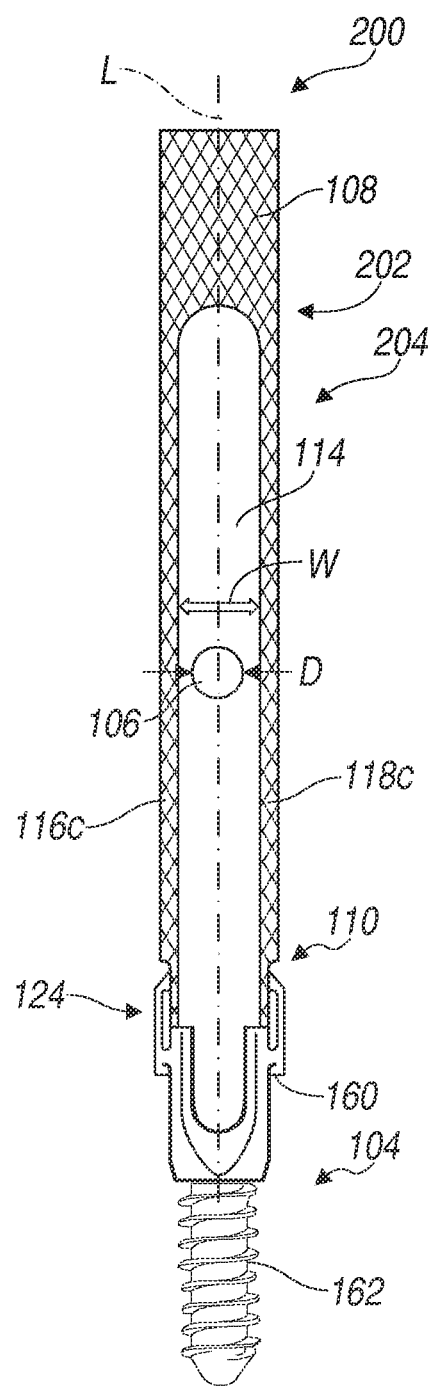
FIG. 13 is a schematic illustration of a front view of another exemplary deformable device for use with a percutaneous fixation system for performing a minimally invasive fixation procedure in a first, retracted state.
Figure 14:
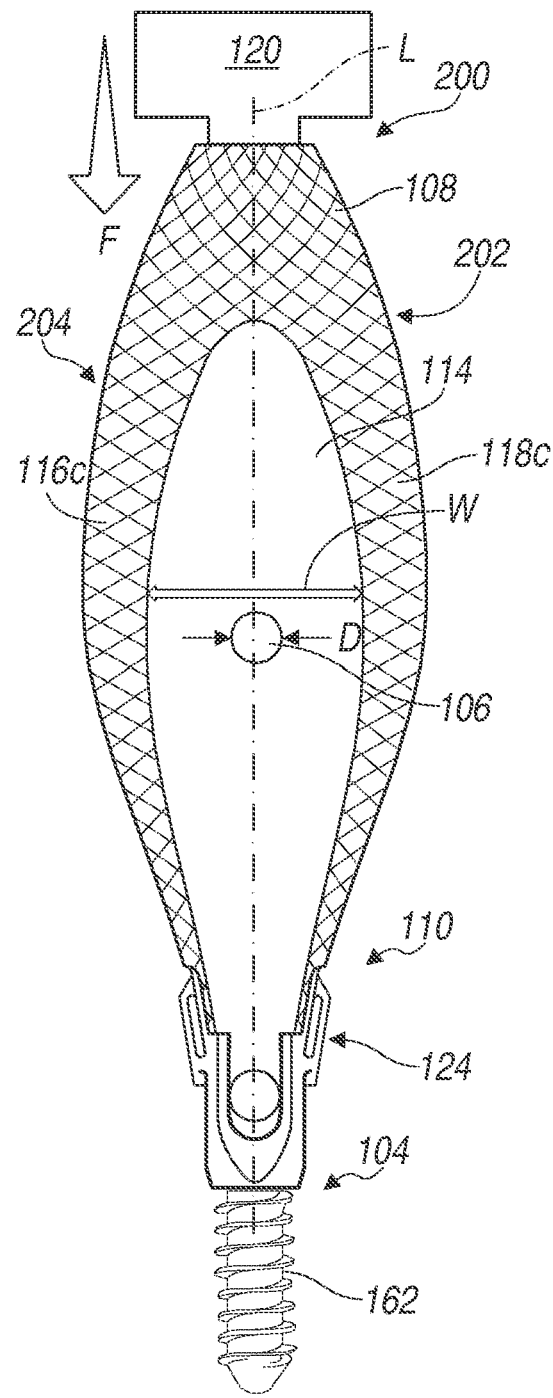
FIG. 14 is a schematic illustration of a front view of the exemplary deformable device of FIG. 13 in a second, expanded state.

With reference now to FIGS. 13 and 14, in one example, a percutaneous fixation system 200 can enable a spinal procedure armed percutaneously in a minimally invasive manner. As the percutaneous fixation system 200 can be similar to the percutaneous fixation system 100 described with reference to FIGS. 1-12, only the differences between the percutaneous fixation system 100 and the percutaneous fixation system 200 will be discussed in great detail herein, and the same reference numerals will be used to denote the same or similar components.

With reference to FIGS. 13 and 14, the percutaneous fixation system 200 can include at least one deformable device or tower 202, at least one bone anchor 104 and the connecting rod 106. Generally, a tower 202 can be coupled to each bone anchor 104 to facilitate coupling the bone anchor 104 to the anatomy. The tower 202 can also guide the connecting rod 106 into engagement with the bone anchor 104, as discussed with regard to the percutaneous fixation system 100. Generally, the tower 202 can comprise hollow cylindrical tubes, however, the tower 202 can have any suitable shape for insertion into the anatomy, such as an hourglass, etc.

The at least one tower 202 can include the throughbore B, the proximal end 108, the distal end 110 and a deformable portion 204. The longitudinal axis L can be defined from the proximal end 108 to the distal end 110, and the channel 114 can be defined through the tower 202 from the proximal end 108 to the distal end 110 about a portion of the longitudinal axis. The formation of the channel 114 can result in the creation of the first leg member 116 and the second leg member 118, which extend generally parallel to the longitudinal axis L, as will be discussed.

The deformable portion 204 of the tower 202 can be formed between the proximal end 108 and distal end 110 of the tower 202, or at a middle portion or midsection of the tower 202. Generally, the deformable portion 204 can be defined on at least a portion of the first leg member 116 and the second leg member 118, and thus, can be formed about the channel 114. The deformable portion 204 can facilitate coupling the connecting rod 106 to the bone anchor 104 by changing a width W of the channel 114. The width W of the channel 114 can be defined in a direction transverse to the longitudinal axis L of the tower 202. The width W of the channel 114 can be changed by moving the deformable portion 204 between a retracted state and an expanded state.

In this regard, the deformable portion 204 can be selectively and reversibly movable between the retracted state and the expanded state. In the retracted state, the width W of the channel 114 can generally be about equal to or less than the diameter D of the connecting rod 106. In one example, the diameter D of the connecting rod 106 can be about 5.5 millimeters (mm). Thus, in the retracted state, the width W of the channel 114 can be about equal to or less than 5.5 millimeters (mm). In the expanded state, the width W of the channel 114 can be about greater than the diameter D of the connecting rod 106, and thus, the width W in the expanded state can be greater than about 5.5 millimeters (mm). In one example, the width W in the expanded state can range from about 5.5 millimeters (mm) to about 19 millimeters (mm). Thus, the width W in the expanded state can be greater than two times the width W of the channel 114 in the expanded state.

The deformable portion 204 can be formed along at least a portion of each of the first leg member 116 and second leg member 118, thereby forming a first deformable leg member 116c and a second deformable leg member 118c. Each of the first deformable leg member 116c and the second deformable leg member 118c can be movable relative to each other from the retracted state to the expanded state. The movement of the first deformable leg member 116c and the second deformable leg member 118c between the retracted state and the expanded state can increase or decrease the width W of the channel 114.

In this regard, the at least one tower 202 can be formed of an interwoven mesh M, such that each of the first deformable leg member 116c and the second deformable leg member 118c can be formed of the interwoven mesh M. The interwoven mesh M can include suitable biocompatible metal, metal alloy or polymeric fibers, woven into a cylindrical biaxial braid, for example. In this example, in order to move the tower 202 from the retracted state (FIG. 13) to the expanded state (FIG. 14), a compressive force F can be applied to the proximal end 108 of the tower 202, which can cause the interwoven fibers of the mesh M to loosen. The loosening of the interwoven fibers f the mesh M can cause the first deformable leg member 116c and the second deformable leg member 118c to expand outwardly, in a direction transverse to the longitudinal axis L of the tower 202. It should be noted that any suitable tool 120 can be used to apply the compressive force F to the tower 202. The removal of the compressive force F from the proximal end 108 of the tower 202 can cause the interwoven fibers the mesh to tighten, thereby moving the first deformable leg member 116c and the second deformable leg member 118c from the expanded state (FIG. 14) to the retracted state (FIG. 13).

As the percutaneous fixation system 200 can be used in the anatomy in the same manner as the percutaneous fixation system 100 discussed with regard to FIGS. 1-12, the use of the percutaneous fixation system 200 in the anatomy will not be discussed in great detail herein. Briefly, however, once each tower 202 is positioned within the anatomy in the retracted state, each tower 202 can be moved into the expanded state by applying the compressive force F to the proximal end 108 of the tower 202. After the connecting rod 106 is coupled to the receiver 160a, the compressive force F can be removed from the proximal end 108 of at least one tower 202 to move the tower 202 from the expanded state to the retracted state. Then, the tower 202 can be removed from the anatomy, as discussed.

Figure 15:
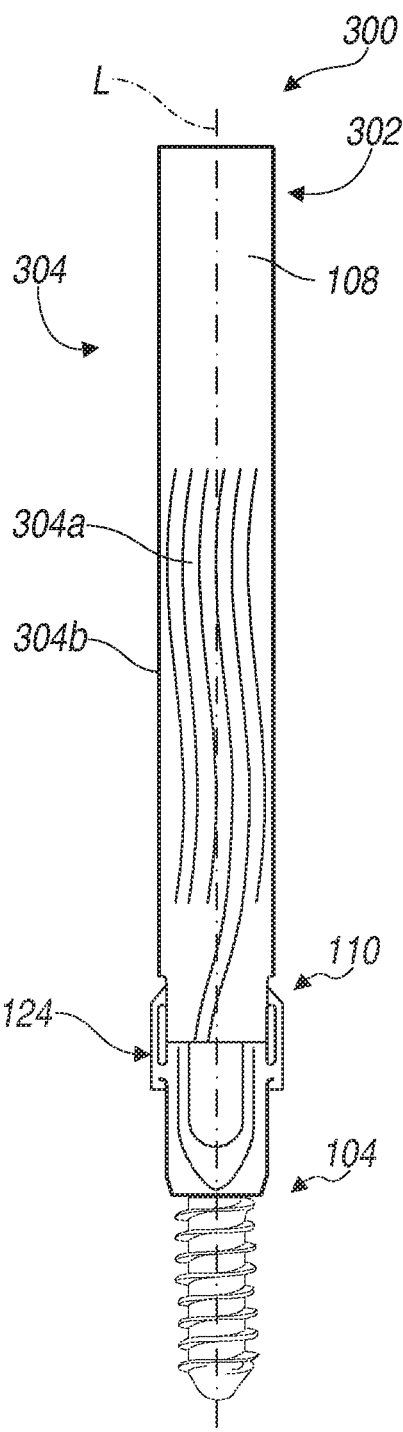
FIG. 15 is a schematic illustration of a front view of another exemplary deformable device for use with a percutaneous fixation system for performing a minimally invasive fixation procedure in a first, retracted state.
Figure 16:
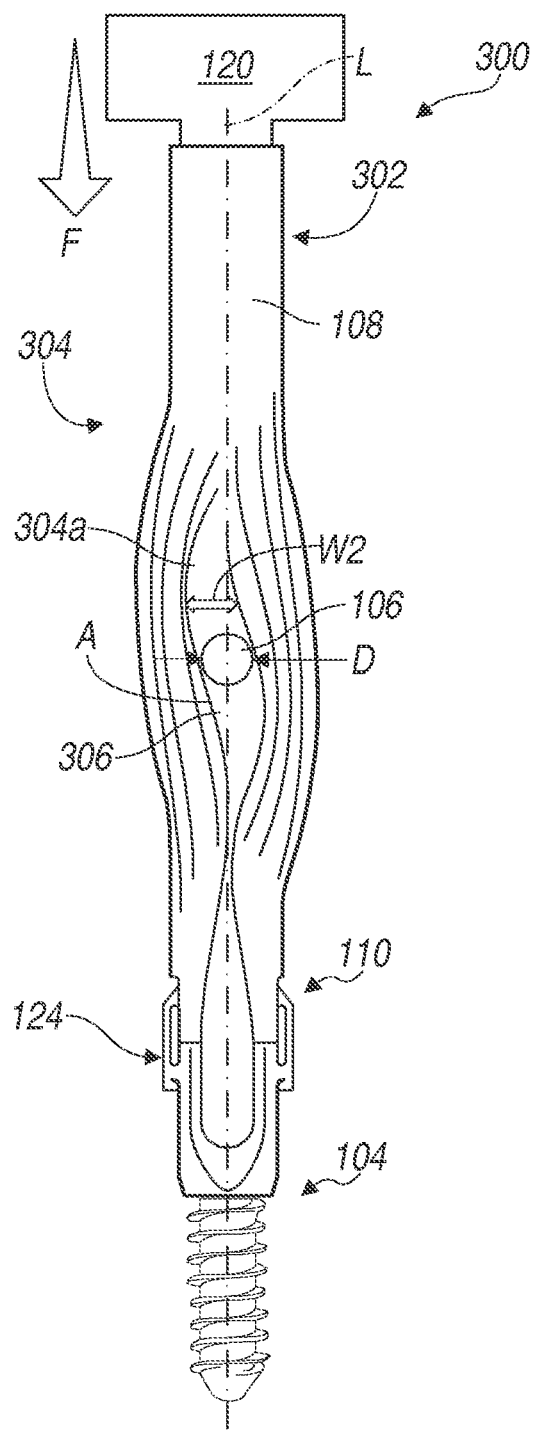
FIG. 16 is a schematic illustration of the exemplary deformable device of FIG. 15 in a second, expanded state.

With reference now to FIGS. 15 and 16, in one example, a percutaneous fixation system 300 can enable a spinal procedure to be performed percutaneously in a minimally invasive manner. As the percutaneous fixation system 300 can be similar to the percutaneous fixation system 100 described with reference to FIGS. 1-12, only the differences between the percutaneous fixation system 100 and the percutaneous fixation system 300 will be discussed in great detail herein, and the same reference numerals will be used to denote the same or similar components.

With reference to FIGS. 15 and 16, the percutaneous fixation system 300 can include at least one deformable devices or tower 302, the at least one bone anchors 104 and the connecting rod 106. Generally, a tower 302 can be coupled to the bone anchor 104 to facilitate coupling the bone anchor 104 to the anatomy. The tower 302 can also guide the connecting rod 106 into engagement with the bone anchor 104, as discussed with regard to the percutaneous fixation system 100. Generally, the tower 302 can comprise hollow cylindrical tubes, however, the tower 302 can have any suitable shape for insertion into the anatomy, such as an hourglass, etc.

The tower 302 can include the throughbore B, the proximal end 108, the distal end 110 and a deformable portion 304. The longitudinal axis L can be defined from the proximal end 108 to the distal end 110. The deformable portion 304 of the tower 302 can be formed between the proximal end 108 and distal end 110 of the tower 302, or at a middle portion or midsection of the tower 302. The deformable portion 304 can include at least one slit 304a. Generally, the deformable portion 304 can include two slits 304a, which can each be formed through a surface 304b. Each slit 304a can be formed through a suitable cutting operation, and in one example, each slit 304a can be formed by using a laser to cut each slit 304a through the surface 304b of the tower 302.

In one example, the slits 304a can be formed opposite each other, such that when the slits 304a are in the expanded state, the slits 304a can define a channel 306 having an axis A substantially perpendicular to the longitudinal axis L. The channel 306 can be similar to the channel 114 described with regard to the percutaneous fixation system 100, and thus, the channel 306 will not be discussed in great detail herein. Briefly, however, the channel 306 can have a width W2 defined in a direction generally transverse to the longitudinal axis L. The width W2 of the channel 306 in the expanded state (FIG. 16) can be greater than the width W2 of the channel 306 in the retracted state (FIG. 15). In one example, the width W2 of the channel 306 in the expanded state (FIG. 16) can be sized to enable the connecting rod 106 to be received therethrough, and in the retracted state (FIG. 15), the width W2 can be sized to enable the tower 302 to be inserted into the anatomy percutaneously in a minimally invasive manner.

For example, in the retracted state, the width W2 of the channel 306 can be about equal to or less than 5.5 millimeters (mm). Generally, the slits 304a can be formed such that in the retracted state, the slits 304a are closed, or the channel 306 has about zero width W2, as shown in FIG. 15. In the expanded state, as shown in FIG. 16, the slits 304a can be opened, such that the width W2 of the channel 306 can be greater than about 5.5 millimeters (mm), and in one example, the width W2 in the expanded state can range from about 5.5 millimeters (mm) to about 19 millimeters. Thus, the width W2 of the channel 306 in the expanded state can be greater than two times the width W2 of the channel 306 in the retracted state.

In this example, in order to move the to tower 302 from the retracted state to the expanded state, a compressive force F can be applied to the proximal end 108 of the tower 302, which can cause the slits 304a to open, thereby forming the channel 306 (FIG. 16). It should be noted that any suitable tool 120 can be used to apply the compressive force F to the tower 302. The removal of the compressive force F from the proximal end 108 of the tower 302 can cause the slits 304a to close into the retracted state (FIG. 15).

As the percutaneous fixation system 300 can be used in the anatomy in the same manner as the percutaneous fixation system 100 discussed with regard to FIGS. 1-12, the use of the percutaneous fixation system 300 in the anatomy will not be discussed in great detail herein. Briefly, however, once each tower 302 is positioned within the anatomy in the retracted state (FIG. 15), each tower 302 can be moved into the expanded state (FIG. 16) by applying the compressive force F to the proximal end 108 of the tower 302. After the connecting rod 106 is coupled to the receiver 160a, the compressive force F can be removed from the proximal end 108 of the tower 302 to move the tower 302 from the expanded state (FIG. 16) to the retracted state (FIG. 15). Then, the tower 302 can be removed from the anatomy, as discussed.

Accordingly, the percutaneous fixation system 100, 200, 300 can enable an orthopedic procedure, such as a spinal fixation or fusion procedure, to be performed in a minimally invasive manner. The use of the towers 102, 202, 302 can enable the formation of a smaller incision in the anatomy, while still facilitating the coupling of the connecting rod to the bone anchors 104. In this regard, by providing each of the towers 102, 202, 302 with a deformable portion 112, 112b, 204, 304 a width of the towers 102, 202, 302 can be minimized in the first, retracted state, and the width of the towers 102, 202, 302 can be maximized in the second, expanded state for accepting the connecting rod 106 therethrough. Thus, the towers 102, 202, 302 can provide a larger passageway for the surgeon to maneuver the connecting rod 106 through the anatomy during a minimally invasive procedure, without requiring a larger incision to be made through the skin S of the patient.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

For example, while the percutaneous fixation system 100 has been described herein as including at least one tower 102, 202, 302 having a deformable portion 112, 112b, 204, 304 movable between a retracted state and an expanded state, those of skill in the art will appreciate that the present disclosure, in its broadest aspects, may be constructed alternatively. In this regard, with reference to FIGS. 17-19, a percutaneous fixation system 400 can include a plurality of implants or bone anchors 402 and the connecting rod 106. Each bone anchor 402 can include a first or proximal end 404 and bone fastener 162. The proximal end 404 can include a deformable member 406. In one example, the deformable member 406 can be formed of a shape memory alloy material, and can be coupled to the proximal end 404 at a first end 406a and a second end 406b. In this example, a midsection or a middle portion 406c of the deformable portion 406 can be defined between the first end 406a and the second end 406b. The middle portion 406c is not directly coupled to the proximal end 404 so that the middle portion 406c of the deformable member 406 can be movable between a retracted state and an expanded state. The deformable member 406 can move from the retracted state to the expanded state via the application of heat or electric current by a suitable tool 120 (FIG. 10).

In the expanded state, shown in FIG. 18, the deformable member 406 can at least partially define a channel 408. The channel 408 can have a width W3. The width W3 defined in a direction generally transverse to the longitudinal axis L.

The width W3 of the channel 408 in the expanded state (FIG. 18) can be greater than the width W3 of the channel 408 in the retracted state (FIG. 17). In one example, the width W3 of the channel 408 in the expanded state (FIG. 18) can be sized to enable the connecting rod 106 to be received therethrough, and in the retracted state (FIG. 1), the width W3 can be sized to enable the bone anchor 402 to be inserted into the anatomy percutaneously in a minimally invasive manner.

For example, in the retracted state, the width W3 of the channel 408 can be about equal to or less than 6.5 millimeters (mm). Generally, the deformable member 406 can be formed such that in the retracted state, the channel 408 has about zero width W3, as shown in FIG. 17. Thus, in the retracted state, the deformable member 406 can be in contact with the proximal end 404 over a length of the deformable member 406. In the expanded state, as shown in FIG. 18, the width W3 of the channel 408 can be greater than about 5.5 millimeters (mm), and in one example, the width W3 in the expanded state can range from about 5.5 millimeters (mm) to about 19 millimeters (mm). Thus, the width W3 of the channel 408 in the expanded state (FIG. 18) can be greater than two times the width W3 of the channel 408 in the retracted state (FIG. 17).

As the percutaneous fixation system 400 can be used in the anatomy in the same manner as the percutaneous fixation system 100 discussed with regard to FIGS. 1-12, the use of the percutaneous fixation system 400 in the anatomy will not be discussed in great detail herein. Briefly, however, once each bone anchor 402 is positioned within the anatomy in the retracted state, heat or electric current can be applied to the first end 406a of the deformable member 406 via the tool 120, which can cause the deformable member 406 to form the channel 408. It should be noted that any suitable tool 120 can be used to apply the heat or electric current to the deformable member 406. With the deformable member 406 in the expanded state, the connecting rod 106 can be positioned through the channel 408. Then, the heat or electric current can be removed from the deformable member 406. The removal of the heat or electric current can cause the deformable member 406 to move into the retracted state, and thereby couple the connecting rod 106 to the bone anchor 104, as shown in FIG. 19.

What is claimed is:

1. A tower for percutaneous rod insertion, the tower comprising:
a elongate body including a proximal end, a distal end, and a deformable portion disposed between the proximal end and the distal end;
the proximal end including a circumferentially closed section forming a complete cylinder portion of the elongate body;
the distal end including a first leg and a second leg couplable to a first arm and a second arm, respectively, of a saddle portion of a pedicle screw; and
the deformable portion including a pair of deformable leg members extending proximally from the first leg and the second leg to the proximal end and defining an expandable channel configured to receive a connecting rod and direct the connecting rod into the saddle portion of the pedicle screw, wherein the expandable channel is configured to expand along a width measured between the first leg and the second leg, the width is measured along an axis transverse to a longitudinal axis running from distal end to the proximal end of the tower.

2. The tower of claim 1, wherein the tower defines a central bore extending along a longitudinal axis from an opening on the proximal end to the distal end forming a passage from the proximal end into the saddle portion of a pedicle screw.

3. The tower of claim 1, wherein the tower is integrally formed with the saddle portion of the pedicle screw.

4. The tower of claim 3, wherein the distal end of the elongate body is frangibly coupled to the first arm and the second arm of the pedicle screw.

5. The tower of claim 4, wherein a frangible notch is formed between each of the first leg and the first arm and the second leg and the second arm.

6. The tower of claim 1, wherein the distal end is releasably coupled to the saddle portion of the pedicle screw through a mating structure selected from the following list of mating structures:
a threaded connection;
a keyed connection; and
a snap-fit connection.

7. The tower of claim 1, wherein the expandable channel of the deformable portion is selectively and reversibly movable between a retracted state and an expanded state.

8. The tower of claim 7, wherein the deformable portion is selectively and reversibly movable between the retracted state and the expanded state through application of a distal form on the proximal end of the elongate body.

9. The tower of claim 7, wherein the deformable portion is formed of a biocompatiable shape memory alloy, and wherein the deformable portion is selectively and reversibly movable between the retracted state and the expanded state through application of heat or an electrical current.

10. The tower of claim 7, wherein with the deformable portion in the expanded state the expandable channel includes a central width greater than a proximal width adjacent the proximal end or a distal width adjacent the distal end.

11. A pedicle screw including an extension for percutaneous rod insertion, the pedicle screw comprising:
a saddle portion including a first arm and a second arm
a cylindrical extension body including a proximal end, a distal end, and a deformable portion disposed between the proximal end and the distal end;
the proximal end including a circumferentially closed section forming a complete cylinder portion of the elongate body;
the distal end including a first leg and a second leg frangibly coupled to the first arm and the second arm of the saddle portion of the pedicle screw; and
the deformable portion including a pair of deformable leg members extending proximally from the first leg and the second leg to the proximal end and defining an expandable channel configured to selectively and reversibly move between an expanded state and a retracted state, wherein the expandable channel is configured to expand between the first leg and the second leg along an axis transverse to a longitudinal axis running from distal end to the proximal end of the tower.

12. The pedicle screw of claim 11, wherein the pair of deformable leg members are spaced apart, and each of pair of deformable leg members further comprises:
a first leg segment at the first end of the pair of deformable leg members;
a second leg segment at the second end of the pair of deformable leg members, the second leg segment connected to the saddle portion;

a first hinge coupled to an end of the first leg segment;

a second hinge coupled to an end of the second leg segment;

a third leg segment coupled to the first hinge at a first end so that the third leg segment is movable relative to the first leg segment via the first hinge;

a third hinge coupled to the third leg segment at a second end;

a fourth leg segment coupled to the third hinge at a first end and coupled to the second hinge at a second end so that the fourth leg segment is movable relative to the second leg segment via the second hinge; and wherein the third leg segment and the fourth leg segment are movable relative to each other via the third hinge to move the first leg member and the second leg member between the expanded state and retracted state, wherein the pair of deformable leg members form an expandable channel, and the expandable channel is configured to expand between the pair of deformable leg members along an axis transverse to a longitudinal axis running from a distal end to a proximal end of the pair of deformable leg members.

13. The pedicle screw of claim 12, wherein the third leg segment and fourth leg segment form a generally acute angle relative to the longitudinal axis in the expanded state.

14. The pedicle screw of claim 11, wherein each one of the pair of deformable leg members is composed of a material that is movable into the expanded state in response to a current directed through the deformable portion and returns to the retracted state when the current is removed from the deformable portion.

15. The pedicle screw of claim 11, wherein each one of the pair of deformable leg members is composed of a material that is movable into the expanded state in response to a compressive force applied to the deformable portion along the longitudinal axis and returns to the retracted state when the compressive force is removed.

16. The pedicle screw of claim 15, wherein the pair of deformable leg members is formed from a cylindrical biaxial braid of a polymeric material, metal material or combinations thereof.

17. The pedicle screw of claim 11, wherein the cylindrical extension body defines a central bore extending along a longitudinal axis from an opening on the proximal end to the distal end forming a passage from the proximal end into the saddle portion of the pedicle screw.

18. A system comprising:

a pedicle screw comprising a saddle housing including a first arm and a second arm; and an extension tower coupled to the saddle housing of the pedicle screw, the extension tower comprising a elongate body that includes a proximal end, a distal end, and a deformable portion disposed between the proximal end and the distal end;

wherein the proximal end includes a circumferentially closed section forming a complete cylinder portion of the elongate body;

wherein the distal end includes a first leg and a second leg couplable to a first arm and a second arm of the saddle housing of the pedicle screw; and wherein the deformable portion includes a pair of deformable leg members extending proximally from the first leg and the second leg to the proximal end and defining an expandable channel configured to receive a connecting rod and direct the connecting rod into the saddle housing of the pedicle screw, wherein the expandable channel is configured to expand between the first leg and the second leg along an axis transverse to a longitudinal axis running from distal end to the proximal end of the tower.

19. The system of claim 18, wherein the expandable channel of the deformable portion is selectively and reversibly movable between a retracted state and an expanded state.

20. The system of claim 19, wherein the deformable portion is selectively and reversibly movable between the retracted state and the expanded state through application of a distal form on the proximal end of the elongate body.

* * * * *